(12) United States Patent
Takano et al.

(10) Patent No.: US 6,410,484 B1
(45) Date of Patent: Jun. 25, 2002

(54) 6-HYDROXY-5,6-DIHYDROURACIL COMPOUND AND HERBICIDAL COMPOSITION CONTAINING THEREOF

(75) Inventors: Minoru Takano, Kameoka; Hirofumi Mishima, Minoo, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 51 days.

(21) Appl. No.: 09/698,211

(22) Filed: Oct. 30, 2000

(30) Foreign Application Priority Data

Nov. 1, 1999 (JP) .......................... 11-310756
Mar. 1, 2000 (JP) ....................... 2000-055432

(51) Int. Cl.$^7$ ................. A01N 43/12; A01N 43/54; A01N 43/84; C07D 239/22
(52) U.S. Cl. ............... 504/221; 504/225; 504/243; 544/52; 544/105; 544/295; 544/309; 544/310; 544/312; 544/314
(58) Field of Search ............... 504/221, 225, 504/243; 544/52, 105, 295, 309, 310, 312, 314

(56) References Cited

U.S. PATENT DOCUMENTS

| | | | |
|---|---|---|---|
| 3,322,526 A | 5/1967 | Loux | 504/240 |
| 3,360,523 A | 12/1967 | Loux | 544/303 |
| 3,843,348 A | * 10/1974 | Lutz et al. | 504/243 |
| 3,925,386 A | * 12/1975 | Jager et al. | 544/253 |
| 4,927,451 A | 5/1990 | Brouwer et al. | 544/309 |

FOREIGN PATENT DOCUMENTS

DE   2 132 763   1/1973
JP   6-92943   4/1994

OTHER PUBLICATIONS

Patent Abstracts of Japan, vol. 007, No. 019, Jan. 25, 1983 (of JP 57–175189).
Patent Abstracts of Japan, vol. 018, No. 361, Jul. 7, 1994 (of JP 06–092,943).

* cited by examiner

*Primary Examiner*—Jeffrey E. Russel
(74) *Attorney, Agent, or Firm*—Sughrue Mion, PLLC

(57) ABSTRACT

A 5,6-dihydrouracil compound given by the formula [I]:

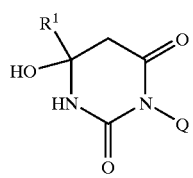

[I]

wherein, $R^1$ represents C1–C2 haloalkyl group and Q represents Q1 of the formula below, etc.:

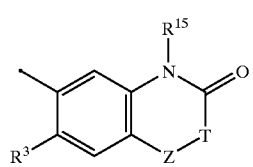

Q1 wherein, $R^3$ is hydrogen atom or halogen atom, $R^{15}$ is C3–C6 alkynyl group, etc., Z is oxygen atom, sulfur atom or NH group, and T is direct bond or methylene group, has an excellent herbicidal efficacy.

17 Claims, No Drawings

6-HYDROXY-5,6-DIHYDROURACIL COMPOUND AND HERBICIDAL COMPOSITION CONTAINING THEREOF

FIELD OF THE INVENTION

The present invention relates to a 5,6-dihydrouracil compound, a herbicidal composition comprising it as an active ingredient, a process for producing it and an intermediate compound for producing it.

BACKGROUND ARTS

At the present time, numerous herbicides are commercially available and they are used. There are, however, many species of weeds to be controlled and their growth extends over a long time. For this reason, requested are herbicides with higher herbicidal activity, wide herbicidal spectrum, and without causing a phytotoxicity problem to crops.

Japanese laid-open patent publication No. Hei06-092943 and U.S. Pat. No. 4,927,451 specification describe a sort of 5,6-dihydrouracil compounds below having a herbicidal activity.

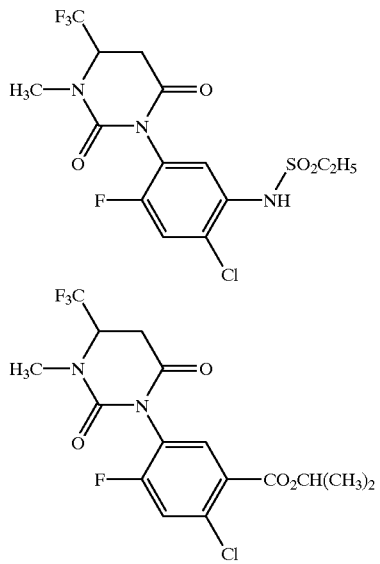

However, the compounds described thereof do not always have sufficient character.

SUMMARY OF THE INVENTION

The object of the present invention is to provide a compound having excellent character as a herbicide.

The present inventors intensively studied to find out compounds having excellent character for herbicides. As a result, they have found that the 5,6-dihydrouracil compounds given by the formula [I] below have excellent character for herbicides, and completed the present invention. Namely, the present invention provides the 5,6-dihydrouracil compound [hereinafter, referred to as the present compound(s)] given by the formula [I]:

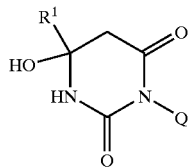

[I]

wherein $R^1$ represents C1–C2 haloalkyl group and Q represents any group of Q1 to Q8 represented by the formulae below:

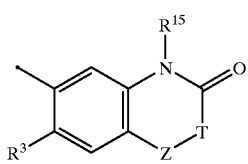

Q1

Q2

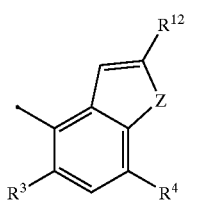

Q3

Q4

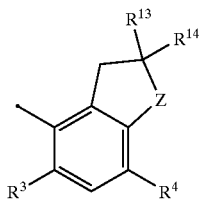

Q5

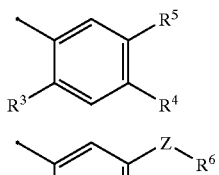

Q6

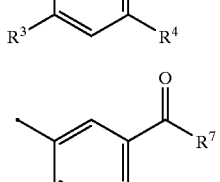

Q7

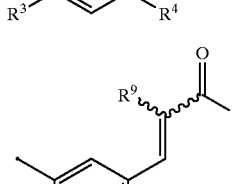

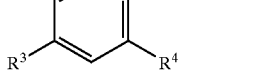

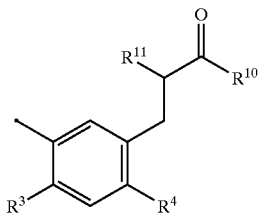

wherein Z represents oxygen atom, sulfur atom or NH group; T represents direct bond or methylene group; $R^3$ represents hydrogen atom or halogen atom; $R^4$ represents hydrogen atom, halogen atom, cyano group, nitro group, ethynyl group or a group given by the formula:

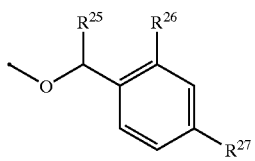

$R^5$ represents hydrogen atom, C1–C6 alkyl group, halogen atom, cyano group, nitro group or hydroxy group; $R^6$ represents C1–C6 alkyl group, C1–C6 haloalkyl group, C3–C8 cycloalkyl group, (C3–C8 cycloalkyl) C1–C3 alkyl group, C3–C6 alkenyl group, C3–C6 alkynyl group, cyano C1–C3 alkyl group, (C1–C3 alkoxy) C1–C3 alkyl group, (C1–C3 alkylthio) C1–C3 alkyl group, (C1–C6 alkyl) carbonyl group, (C1–C6 haloalkyl)carbonyl group, (C3–C8 cycloalkyl)carbonyl group, carboxy C1–C3 alkyl group, (C1–C6 alkoxy)carbonyl C1–C3 alkyl group, (C1–C6 haloalkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, C1–C3 alkoxy (C1–C3 alkoxy)carbonyl C1–C3 alkyl group, carboxy (C1–C3 alkoxy)carbonyl C1–C3 alkyl group, (C1–C6 alkoxy)carbonyl (C1–C3 alkoxy)carbonyl C1–C3 alkyl group, (C1–C6 haloalkoxy)carbonyl (C1–C3 alkoxy) carbonyl C1–C3 alkyl group, (C3–C6 alkenyloxy)carbonyl (C1–C3 alkoxy)carbonyl C1–C3 alkyl group, (C3–C6 alkynyloxy)carbonyl (C1–C3 alkoxy)carbonyl C1–C3 alkyl group, (C3–C8 cycloalkoxy)carbonyl (C1–C3 alkoxy) carbonyl C1–C3 alkyl group, optionally substituted aryloxycarbonyl C1–C3 alkyl group, optionally substituted aryl (C1–C3 alkoxy)carbonyl C1–C3 alkyl group, (C1–C6 alkoxy)carbonyl group, or a group given by the formula $-SO_2R^{17}$, $-C(R^{28})R^{29}CON(R^{21})R^{22}$, $-C(R^{30})R^{31}COON(R^{23})R^{24}$

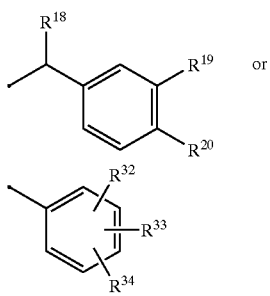

; $R^7$ represents hydrogen atom, C1–C6 alkyl group, C1–C6 haloalkyl group, C3–C8 cycloalkyl group, hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, carboxy C1–C3 alkoxy group, (C1–C6 alkoxy)carboxy C1–C3 alkoxy group, (C3–C8 cycloalkoxy)carboxy C1–C3 alkoxy group, (C3–C6 alkenyloxy)carboxy C1–C3 alkoxy group, (C3–C6 alkynyloxy)carboxy C1–C3 alkoxy group, optionally substituted phenoxy group, optionally substituted benzyloxy group, or a group given by the general formula $-N(R^{21})R^{22}$ or $-ON(R^{23})R^{24}$; $R^8$ represents hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, optionally substituted phenoxy group, optionally substituted benzyloxy group, or a group given by the formula $-N(R^{21})R^{22}$ or $-ON(R^{23})R^{24}$; $R^9$ represents hydrogen atom or halogen atom; $R^{10}$ represents hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, optionally substituted phenoxy group, optionally substituted benzyloxy group, or a group given by the general formula $-N(R^{21})R^{22}$ or $-ON(R^{23})R^{24}$; $R^{11}$ represents hydrogen atom or halogen atom; $R^{12}$ represents hydrogen atom, formyl group, cyano group, nitro group, amino group, C1–C6 alkyl group, C1–C6 haloalkyl group, hydroxy C1–C3 alkyl group, (C1–C3 alkoxy) C1–C3 alkyl group, (C1–C6 alkyl)carbonyloxy C1–C3 alkyl group, (C1–C6 haloalkyl)carbonyloxy C1–C3 alkyl group, carboxy group, (C1–C6 alkoxy)carbonyl group, (C1–C6 haloalkoxy) carbonyl group, (C3–C8 cycloalkoxy)carbonyl group, (C3–C6 alkenyloxy)carbonyl group, (C3–C6 alkynyloxy) carbonyl group or C1–C3 alkoxy (C1–C3 alkoxy)carbonyl group; $R^{13}$ represents hydrogen atom or C1–C3 alkyl group; $R^{14}$ represents hydrogen atom, C1–C6 alkyl group, C1–C6 haloalkyl group, hydroxy C1–C3 alkyl group, (C1–C3 alkoxy) C1–C3 alkyl group, (C1–C6 alkyl)carbonyloxy C1–C3 alkyl group, (C1–C6 haloalkyl)carbonyloxy C1–C3 alkyl group, carboxy group, (C1–C6 alkoxy)carbonyl group, (C1–C6 haloalkoxy)carbonyl group, (C3–C8 cycloalkoxy) carbonyl group, (C3–C6 alkenyloxy)carbonyl group, (C3–C6 alkynyloxy)carbonyl group or C1–C3 alkoxy (C1–C3 alkoxy)carbonyl group; $R^{15}$ represents C1–C6 alkyl group, C1–C6 haloalkyl group, C3–C8 cycloalkyl group, (C3–C8 cycloalkyl) C1–C3 alkyl group, C3–C6 alkenyl group, C3–C6 alkynyl group, cyano C1–C3 alkyl group, (C1–C3 alkoxy) C1–C3 alkyl group, (C1–C3 alkylthio) C1–C3 alkyl group, (C1–C6 alkyl)carbonyl group, (C1–C6 haloalkyl)carbonyl group, (C3–C8 cycloalkyl)carbonyl group, carboxy C1–C3 alkyl group, (C1–C6 alkoxy) carbonyl C1–C3 alkyl group, (C1–C6 haloalkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, C1–C3 alkoxy (C1–C3 alkoxy)carbonyl C1–C3 alkyl group, carboxy (C1–C3 alkoxy)carbonyl C1–C3 alkyl group, (C1–C6 alkoxy)carbonyl (C1–C3 alkoxy)carbonyl C1–C3 alkyl group, (C1–C6 haloalkoxy)carbonyl (C1–C3 alkoxy) carbonyl C1–C3 alkyl group, (C3–C8 cycloalkoxy)carbonyl (C1–C3 alkoxy)carbonyl C1–C3 alkyl group, (C3–C6 alkenyloxy)carbonyl (C1–C3 alkoxy)carbonyl C1–C3 alkyl group, (C3–C6 alkynyloxy)carbonyl (C1–C3 alkoxy) carbonyl C1–C3 alkyl group, optionally substituted aryloxycarbonyl C1–C3 alkyl group, optionally substituted aryl (C1–C3 alkyloxy)carbonyl C1–C3 alkyl group, (C1–C6 alkoxy)carbonyl group or a group given by the formula:

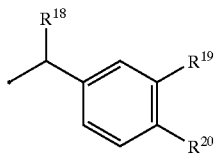

wherein $R^{17}$ represents C1–C3 alkyl group or C1–C3 haloalkyl group; $R^{18}$ represents hydrogen atom, C1–C3 alkyl group or (C1–C6 alkoxy)carbonyl group; $R^{19}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{20}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{21}$ and $R^{22}$ independently represent hydrogen atom or C1–C3 alkyl group, or combined together at their terminal ends to form C2–C5 alkylene group or (C1–C3 alkyleneoxy)C1–C3 alkylene group; $R^{23}$ and $R^{24}$ independently represent hydrogen atom or C1–C3 alkyl group, or combined together at their terminal ends to form C2–C5 alkylene group or (C1–C3 alkyleneoxy) C1–C3 alkylene group; $R^{25}$ represents hydrogen atom, C1–C3 alkyl group or (C1–C6 alkoxy)carbonyl group; $R^{26}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{27}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{28}$ represents hydrogen atom or C1–C3 alkyl group; $R^{29}$ represents hydrogen atom or C1–C3 alkyl group; $R^{30}$ represents hydrogen atom or C1–C3 alkyl group; $R^{31}$ represents hydrogen atom or C1–C3 alkyl group; $R^{32}$, $R^{33}$ and $R^{34}$ are the same or different and represent hydrogen atom, halogen atom, C1–C3 alkyl group, C1–C3 haloalkyl group, nitro group, amino group, hydroxy group, mercapto group, cyano group, carboxy group, (C1–C6 alkoxy)carbonyl group, (C3–C8 cycloalkoxy)carbonyl group, (C3–C6 alkenyloxy)carbonyl group, (C3–C6 alkynyloxy)carbonyl group, carboxy C1–C3 alkyl group, (C1–C6 alkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group, (C3–C6 alkynyloxy)carbonyl C1–C3 alkoxy group, carboxy C1–C3 alkylthio group, (C1–C6 alkoxy)carbonyl C1–C3 alkylthio group, (C3–C8 cycloalkoxy)carbonyl C1–C3 alkylthio group, (C3–C6 alkenyloxy)carbonyl C1–C3 alkylthio group, (C3–C6 alkynyloxy)carbonyl C1–C3 alkylthio group, carboxy C1–C3 alkylamino group, (C1–C6 alkoxy)carbonyl C1–C3 alkylamino group, (C3–C8 cycloalkoxy)carbonyl C1–C3 alkylamino group, (C3–C6 alkenyloxy)carbonyl C1–C3 alkylamino group, (C3–C6 alkynyloxy)carbonyl C1–C3 alkylamino group, C1–C6 alkoxy group, C3–C6 alkenyloxy group, C3–C6 alkynyloxy group, (C1–C6 alkyl)carbonyloxy group, (C1–C6 alkoxy)carbonyloxy group, C1–C6 alkylthio group, C3–C6 alkenylthio group, C3–C6 alkynylthio group, (C1–C6 alkyl)carbonylthio group, (C1–C6 alkoxy)carbonylthio group, C1–C6 alkylamino group, C3–C6 alkenylamino group, C3–C6 alkynylamino group, (C1–C6 alkyl)carbonylamino group or (C1–C6 alkoxy)carbonylamino group, and a herbicidal composition comprising it as an active ingredient. Further, it also gives a process for producing the present compound and an intermediate compound for the production.

The substituents described as "optionally substituted" above are exemplified by halogen atom, C1–C6 alkyl group, C1–C6 alkoxy group, C1–C6 haloalkyl group, C1–C6 haloalkoxy group, nitro group, cyano group, (C1–C6 alkoxy)carbonyl group, (C1–C6 alkoxy)carbonyl C1–C3 alkyl group and (C1–C6 alkoxy)carbonyl C1–C3 alkoxy group.

DETAILED DESCRIPTION OF THE INVENTION

In the present invention, the C1–C2 haloalkyl group represented by $R^1$ may include trifluoromethyl group, chlorodifluoromethyl group, difluoromethyl group and pentafluoroethyl group. The halogen atom represented by $R^3$ may include fluorine atom, chlorine atom, bromine atom and iodine atom. The halogen atom represented by $R^4$ may include fluorine atom, chlorine atom, bromine atom and iodine atom. The C1–C6 alkyl group represented by $R^5$ may include methyl group, ethyl group, propyl group, isopropyl group, butyl group, isobutyl group, sec-butyl group and t-butyl group; and the halogen atom represented by $R^5$ may include fluorine atom, chlorine atom, bromine atom and iodine atom. The C1–C6 alkyl group represented by $R^6$ may include methyl group, ethyl group, propyl group, isopropyl group, butyl group, isobutyl group, sec-butyl group, tert-butyl group, pentyl group and hexyl group; the C1–C6 haloalkyl group represented by $R^6$ may include trifluoromethyl group, difluoromethyl group, 2-fluoroethyl group, 2-chloroethyl group and 2-bromoethyl group; the C3–C8 cycloalkyl group represented by $R^6$ may include cyclopropyl group, cyclobutyl group, cyclopentyl group and cyclohexyl group; the (C3–C8 cycloalkyl) C1–C3 alkyl group represented by $R^6$ may include cyclopropylmethyl group, cyclobutylmethyl group, cyclopentylmethyl group and cyclohexylmethyl group; the C3–C6 alkenyl group represented by $R^6$ may include allyl group, 1-methyl-2-propenyl group, 2-methyl-2-propenyl group and 1,1-dimethyl-2-propenyl group; the C3–C6 alkynyl group represented by $R^6$ may include propargyl group, 1-methy-2-propynyl group, 2-butynyl group and 1,1-dimethyl-2-propynyl group; the cyano C1–C3 alkyl group represented by $R^6$ may include cyanomethyl group, 1-cyanoethyl group, 2-cyanoethyl group and 1-methyl-2-cyanoethyl group; the (C1–C3 alkoxy) C1–C3 alkyl group represented by $R^6$ may include methoxymethyl group, 2-methoxyethyl group, ethoxymethyl group and 2-ethoxyethyl group; the (C1–C3 alkylthio) C1–C3 alkyl group represented by $R^6$ may include methylthiomethyl group, 2-ethylthioethyl group and 2-methylthioethyl group; the (C1–C6 alkyl)carbonyl group represented by $R^6$ may include acetyl group, propionyl group, butyryl group, isobutyryl group and pivaloyl group; the (C1–C6 haloalkyl)carbonyl group represented by $R^6$ may include trifluoroacetyl group, difluoroacetyl group, trichloroacetyl group and dichloroacetyl group; the (C3–C8 cycloalkyl)carbonyl group represented by $R^6$ may include cyclopropylcarbonyl group, cyclopentylcarbonyl group and cyclohexylcarbonyl group; the carboxy C1–C3 alkyl group represented by $R^6$ may include carboxymethyl group, 1-carboxyethyl group, 1-methyl-1-carboxyethyl group, 1-carboxypropyl group, 2-carboxyethyl group and 1-methyl-2-carboxylethyl group; the (C1–C6 alkoxy) carbonyl C1–C3 alkyl group represented by $R^6$ may include methoxycarbonylmethyl group, ethoxycarbonylmethyl group, propoxycarbonylmethyl group, isopropoxyearbonylmethyl group, butoxycarbonylmethyl group, isobutoxycarbonylmethyl group, sec-butoxycarbonylmethyl group, tert-butoxycarbonylmethyl group, pentyloxycarbonylmethyl group, isopentyloxycarbonylmethyl group, hexyloxycarbonylmethyl group, isohexyloxycarbonylmethyl group, 1-methoxycarbonylethyl group, 1-ethoxycarbonylethyl group, 1-(propoxycarbonyl)ethyl group, 1-(isopropoxycarbonyl)ethyl group, 1-(butoxycarbonyl) ethyl group, 1-(isobutoxycarbonyl)ethyl group, 1-(sec-butoxycarbonyl)ethyl group, 1-(tert-butoxycarbonyl)ethyl group, 1-(pentyloxycarbonyl)ethyl group, 1-isopentyloxycarbonyl)ethyl group, 1-(hexyloxycarbonyl) ethyl group, 1-(isohexyloxycarbonyl)ethyl group, 1-methyl-1-(methoxycarbonyl)ethyl group, 1-methyl-1-(ethoxycarbonyl)ethyl group, 1-methyl-1-(propoxycarbonyl)ethyl group, 1-methyl-1-(isopropoxycarbonyl)ethyl group, 1-methyl-1-butoxycarbonyl)ethyl group, 1-methyl-1-(isobutoxycarbonyl)ethyl group, 1-methyl-1-(sec-butoxycarbonyl)ethyl group, 1-methyl-l-(tert-butoxycarbonyl)ethyl group, 1-methyl-1-(pentyloxycarbonyl)ethyl group, 1-methyl-1-(isopentyloxycarbonyl)ethyl group, 1-methyl-1-(hexyl oxycarbonyl)ethyl group and 1-methyl-1-(isohexyloxycarbonyl)ethyl group; the (C1–C6 haloalkoxy) carbonyl C1–C3 alkyl group represented by $R^6$ may include 2-fluoroethoxycarbonylmethyl group, 2-chloroethoxycarbonylmethyl group, 2-bromoethoxycarbonylmethyl group, 2,2,2-trifluoroethoxycarbonylmethyl group, 1-(2-fluoroethoxycarbonyl)ethyl group, 1-(2-chloroethoxycarbonyl)ethyl group, 1-(2-bromoethoxycarbonyl)ethyl group, 1-(2,2,2-trifluoroethoxycarbonyl)ethyl group, 1-methyl-1-(2-fluoroethoxycarbonyl)ethyl group, 1-methyl-1-(2-chloroethoxycarbonyl)ethyl group, 1-methyl-1-(2-bromoethoxycarbonyl)ethyl group and 1-methyl-1-(2,2,2-trifluoroethoxycarbonyl)ethyl group; the (C3–C8 cycloalkoxy)carbonyl C1–C3 alkyl group represented by $R^6$ may include cyclopropoxycarbonylmethyl group, cyclobutoxyearbonylmethyl group, cyclopentyloxycarbonylmethyl group, cyclohexyloxycarbonylmethyl group, 1-cyclopropoxycarbonylethyl group, 1-cyclobutoxycarbonylethyl group, 1-cyclopentyloxycarbonylethyl group, 1-cyclohexyloxycarbonylethyl group, 1-methyl-1-(cyclopropoxycarbonyl)ethyl group, 1-methyl-1-(cyclobutoxycarbonyl)ethyl group, 1-methyl-1-(cyclopentyloxycarbonyl)ethyl group and 1-methyl-1-(cyclohexyloxycarbonyl)ethyl group; the (C3–C6 alkenyloxy)carbonyl C1–C3 alkyl group represented by $R^6$ may include allyloxycarbonylmethyl group, 1-methyl-2-propenyloxycarbonylmethyl group, 2-methyl-2-propenyloxycarbonylmethyl group, 1,1-dimethyl-2-propenyloxycarbonylmethyl group, 1-(allyloxycarbonyl) ethyl group, 1-(1-methyl-2-propenyloxycarbonyl)ethyl group, 1-(2-methyl-2-propenyloxycarbonyl)ethyl group, 1-(1,1-dimethyl-2-propenyloxycarbonyl)ethyl group, 1-methyl-1-(allyloxycarbonyl)ethyl group, 1-methyl-1-(1-methyl-2-propenyloxycarbonyl)ethyl group, 1-methyl-1-(2-methyl-2-propenyloxycarbonyl)ethyl group and 1-methyl-1-(1,1-dimethyl-2-propenyloxycarbonyl)ethyl group; the (C3–C6 alkynyloxy)carbonyl C1–C3 alkyl group represented by $R^6$ may include propargyloxycarbonyl)ethyl group, 1-methyl-2-propynyloxycarbonylmethyl group, 2-butynyloxycarbonylmethyl group, 1,1-dimethyl-2-propynyloxycarbonylmethyl group, 1-(propargyloxycarbonyl)ethyl group, 1-(1-methyl-2-propynyloxycarbonyl)ethyl group, 1-(2-butynyloxycarbonyl)ethyl group, 1-(1, 1-dimethyl-2-propynyloxycarbonyl)ethyl group, 1-methyl-1-(propargyloxycarbonyl)ethyl group, 1-methyl-1-(1-methyl-2-propynyloxycarbonyl)ethyl group, 1-methyl-1-(2-butynyloxycarbonyl)ethyl group and 1-methyl-1-(1,1-dimethyl-2-propynyloxycarbonyl)ethyl group; the C1–C3 alkoxy (C1–C3 alkoxy)carbonyl C1–C3 alkyl group represented by $R^6$ may include methoxymethoxycarbonylmethyl group, 2-methoxyethoxycarbonylmethyl group, ethoxymethoxycarbonylmethyl group, 2-ethoxyethoxycarbonylmethyl group, 1-(methoxymethoxycarbonyl)ethyl group, 1-(2-methoxyethoxycarbonyl)ethyl group, 1-(ethoxymethoxycarbonyl)ethyl group, 1-(2-ethoxyethoxycarbonyl)ethyl group, 1-methyl-1-(methoxymethoxycarbonyl)ethyl group, 1-methyl-1-(2-methoxyethoxycarbonyl)ethyl group, 1-methyl-1-(ethoxymethoxycarbonyl)ethyl group and 1-methyl-1-(2-ethoxyethoxycarbonyl)ethyl group; the carboxy (C1–C3 alkoxy)carbonyl C1–C3 alkyl group represented by $R^6$ may include carboxymethoxycarbonylmethyl group, 1-(carboxy)ethoxycarbonylmethyl group, 1-(carboxymethoxycarbonyl) ethyl group, 1-{1-(carboxy)ethoxycarbonyl}ethyl group, 1-methyl-1-(carboxy)ethoxycarbonylmethyl group and 1-{1-methyl-1-(carboxy)ethoxycarbonyl}ethyl group; the (C1–C6 alkoxy)carbonyl (C 1–C3 alkoxy)carbonyl C1–C3 alkyl group represented by $R^6$ may include methoxycarbonylmethoxycarbonylmethyl group, 1-(methoxycarbonyl) ethoxycarbonylmethyl group, 1-(methoxycarbonylmethoxycarbonyl)ethyl group, 1-{1-(methoxycarbonyl)ethoxycarbonyl}ethyl group, 1-methyl-1-(methoxycarbonyl)ethoxycarbonylmethyl group, 1-{1-methyl-1-(methoxycarbonyl)ethoxycarbonyl}ethyl group, ethoxycarbonylmethoxycarbonylmethyl group, 1-(ethoxycarbonyl)ethoxycarbonylmethyl group, 1-(ethoxycarbonylmethoxycarbonyl)ethyl group, 1-{1-(ethoxycarbonyl)ethoxycarbonyl}ethyl group, 1-methyl-1-(ethoxycarbonyl)ethoxycarbonylmethyl group and 1-{1-methyl-1-(ethoxycarbonyl)ethoxycarbonyl}ethyl group; the (C1–C6 haloalkoxy)carbonyl (C1–C3 alkoxy)carbonyl C1–C3 alkyl group represented by $R^6$ may include 2-fluoroethoxycarbonylmethoxycarbonylmethyl group, 1-(2-fluoroethoxyearbonyl)ethoxycarbonylmethyl group, 1-(2-fluoroethoxycarbonylmethoxycarbonyl)ethyl group, 1-{1-(2-fluoroethoxycarbonyl)ethoxycarbonyl}ethyl group, 1-methyl-2-(2-fluoroethoxycarbonyl)ethoxycarbonylmethyl group, 1-{1-methyl-1-(2-fluoroethoxycarbonyl) ethoxycarbonyl}ethyl group, 2-chloroethoxycarbonylmethoxycarbonylmethyl group, 1-(2-chloroethoxycarbonyl)ethoxycarbonylmethyl group, 1-(2-chloroethoxycarbonylmethoxycarbonyl)ethyl group, 1-{1-(2-chloroethoxycarbonyl)ethoxycarbonyl}ethyl group, 1-methyl-1-(2-chloroethoxycarbonyl) ethoxycarbonylmethyl group and 1-{methyl-1-(2-chloroethoxycarbonyl)ethoxycarbonyl}ethyl group; the (C3–C6 alkenyloxy)carbonyl (C1–C3 alkoxy)carbonyl C1–C3 alkyl group represented by $R^6$ may include allyloxycarbonylmethoxycarbonylmethyl group, 1-(allyloxycarbonyl)ethoxycarbonylmethyl group, 1-(allyloxycarbonylmethoxycarbonyl)ethyl group, 1-{(1-(alyloxycarbonyl)ethoxycarbonyl}ethyl group, 1-methyl-1-(allyloxycarbonyl)ethoxycarbonylmethyl group and 1-{1-methyl-1-(allyloxycarbonyl)ethoxycarbonyl}ethyl group; the (C3–C6 alkynyloxy)carbonyl (C1–C3 alkoxy)carbonyl C1–C3 alkyl group represented by $R^6$ may include propargyloxycarbonylmethoxycarbonylmethyl group, 1-(propargyloxycarbonyl)ethoxycarbonylmethyl group, 1-(propargyloxycarbonylmethoxycarbonyl)ethyl group, 1-{1-(propargyloxycarbonyl)ethoxycarbonyl}ethyl group, 1-methyl-1-(propargyloxycarbonyl)ethoxycarbonylmethyl group and 1-{1-methyl-1-(propargyloxycarbonyl) ethoxycarbonyl}ethyl group; the (C3–C8 cycloalkoxy) carbonyl (C1–C3 alkoxy)carbonyl C1–C3 alkyl group represented by $R^6$ may include cyclopentyloxycarbonylmethoxycarbonylmethyl group, 1-(cyclopentyloxycarbonyl)ethoxycarbonylmethyl group, 1-(cyclopentyloxycarbonylmethoxycarbonyl)ethyl group, 1-{1-(cyclopentyloxycarbonyl)ethoxycarbonyl}ethyl group, 1-methyl-1-(cyclopentyloxycarbonyl) ethoxycarbonylmethyl group and 1-{1-methyl-1-(cyclopentyloxycarbonyl)ethoxycarbonyl}ethyl group; the optionally substituted aryloxycarbony C1–C3 alkyl group represented by $R^6$ may include phenoxycarbonylmethyl group, 1-phenoxycarbonylethyl group and 1-methyl-1-(phenoxycarbonyl)ethyl group; the optionally substituted aryl (C1–C3 alkoxy)carbony C1–C3 alkyl group represented by $R^6$ may include benzyloxycarbonylmethyl group, 1-benzyloxycarbonylethyl group, 1-methyl-1-(benzyloxycarbonyl)ethyl group, phenethyloxycarbonylmethyl group, 1-phenethyloxycarbonylethyl group and 1-methyl-1-(phenethyloxycarbonyl)ethyl group; and the (C1–C6 alkoxy)carbony group represented by $R^6$ may include methoxycarbonyl group, ethoxycarbonyl group, propoxycarbonyl group and isopropoxycarbonyl group. The C1–C6 alkyl group represented by $R^7$ may include methyl group, ethyl group, propyl group, isopropyl group, butyl group, isobutyl group, sec-butyl group, tert-butyl group, pentyl group and hexyl group; the C1–C6 haloalkyl group represented by $R^7$ may include trifluoromethyl group, difluoromethyl group, 2-fluoroethyl group, 2-chloroethyl group and 2-bromoethyl group; the C3–C8 cycloalkyl group represented by $R^7$ may include cyclopropyl group, cyclobutyl group, cyclopentyl group and cyclohexyl group; the C1–C6 alkoxy group represented by $R^7$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^7$ may include 2-fluoroethoxy group, 2-chloroethoxy group and 2-bromoethoxy group; the C3–C8 cycloalkoxy group represented by $R^7$ may include cyclopropoxy group, cyclobutoxy group, cyclopentyloxy group and cyclohexyloxy group; the C3–C6 alkenyloxy group represented by $R^7$ may include allyloxy group, 1-methyl-2-propenyloxy group, 2- methyl-2-propenyloxy group and 1,1-dimethyl-2-propenyloxy group; the C3–C6 alkynyloxy group represented by $R^7$ may include propargyloxy group, 1-methyl-2-propynyloxy group, 2-butynyloxy group and 1,1-dimethyl-2-propynyloxy group; the (C1–C3 alkoxy) C1–C3 alkoxy group represented by $R^7$ may include methoxymethoxy group, 2-methoxyethoxy group, ethoxymethoxy group and so on; the carboxy C1–C3 alkoxy group represented by $R^7$ may include carboxymethoxy group, 1-carboxyethoxy group and 1-methyl-1-(carboxy)ethoxy group; the (C1–C6 alkoxy) carbonyl C1–C3 alkoxy group represented by $R^7$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1-(propoxycarbonyl)ethoxy group, 1-(isopropoxycarbonyl)ethoxy group, 1-(butoxycarbonyl) ethoxy group, 1-(isobutoxycarbonyl)ethoxy group, 1-(sec-butoxycarbonyl)ethoxy group, 1-(tert-butoxycarbonylpethoxy group, 1-(pentyloxycarbonyl) ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxycarbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl)ethoxy group, 1-methyl-1-(isopentyloxycarbonyl)ethoxy group, 1-methyl-1-(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^7$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^7$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl) ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; the (C3–C6 alkynyloxy)carbonyl C1–C3 alkoxy group represented by $R^7$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group; the optionally substituted phenoxy group represented by $R^7$ may include phenoxy group; and the optionally substituted benzyloxy group represented by $R^7$ may include benzyloxy group. The C1–C6 alkoxy group represented by $R^8$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^8$ may include 2-fluoroethoxy group, 2-chloroethoxy group, 2-bromoethoxy group and so on; the C3–C8 cycloalkoxy group represented by $R^8$ may include cyclopropoxy group, cyclobutoxy group, cyclopentyloxy group and cyclohexyloxy group; the C3–C6 alkenyloxy group represented by $R^8$ may include allyloxy group, 1-methyl-2-propenyloxy group, 2-methyl-2-propenyloxy group and 1,1-dimethyl-2-propenyloxy group; the C3–C6 alkynyloxy group represented by $R^8$ may include propargyloxy group, 1-methyl-2-propynyloxy group, 2-butynyloxy group and 1,1-dimethyl-2-propynyloxy group; the (C1–C3 alkoxy) C1–C3 alkoxy group represented by $R^8$ may include methoxymethoxy group, 2-methoxyethoxy group and ethoxymethoxy group; the optionally substituted phenoxy group represented by $R^8$ may include phenoxy group; and the optionally substituted benzyloxy group represented by $R^8$ may include benzyloxy group. The halogen atom represented by $R^9$ may include chlorine atom and bromine atom. The C1–C6 alkoxy group represented by $R^{10}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{10}$ may include 2-fluoroethoxy group, 2-chloroethoxy group and 2-bromoethoxy group; the C3–C8 cycloalkoxy group represented by $R^{10}$ may include cyclopropoxy group, cyclobutoxy group, cyclopentyloxy group and cyclohexyloxy group; the C3–C6 alkenyloxy group represented by $R^{10}$ may include allyloxy group, 1-methyl-2-propenyloxy group, 2-methyl-2-propenyloxy group and 1,1-dimethyl-2-propenyloxy group; the C3–C6 alkynyloxy group represented by $R^{10}$ may include propargyloxy group, 1-methyl-2-propynyloxy group, 2-butynyloxy group and 1,1-dimethyl-2-propynyloxy group; the (C1–C3 alkoxy) C1–C3 alkoxy group represented by $R^{10}$ may include methoxymethoxy group, 2-methoxyethoxy group and ethoxymethoxy group; the optionally substituted phenoxy group represented by $R^{10}$ may include phenoxy group; and the optionally substituted benzyloxy group represented by $R^{10}$ may include benzyloxy group. The halogen atom represented by $R^{11}$ may include chlorine atom and bromine atom. The C1–C6 alkyl group represented by $R^{12}$ may include methyl group, ethyl group and isopropyl group; the C1–C6 haloalkyl group represented by $R^{12}$ may include chloromethyl group, bromomethyl group, fluoromethyl group, dichloromethyl group, dibromomethyl group and difluoromethyl group; the hydroxy C1–C3 alkyl group represented by $R^{12}$ may include hydroxymethyl group and 2-hydroxyethyl group; the (C1–C3 alkoxy) C1–C3 alkyl group represented by $R^{12}$ may include methoxymethyl group, ethoxymethyl group and isopropoxymethyl group; the (C1–C6 alkyl)carbonyloxy C1–C3 alkyl group represented by $R^{12}$ may include methylcarbonyloxymethyl group and ethylcarbonyloxymethyl group; the (C1–C6 haloalkyl) carbonyloxy C1–C3 alkyl group represented by $R^{12}$ may include trifluoroacetoxymethyl group and difluoroacetoxymethyl group; the (C1–C6 alkoxy)carbonyl group represented by $R^{12}$ may include methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group and hexyloxycarbonyl group; the (C1–C6 haloalkoxy)carbonyl group represented by $R^{12}$ may include 2,2,2-trifluoroethoxycarbonyl group, 2-fluoroethoxycarbonyl group, 2-chloroethoxycarbonyl group and 2-bromoethoxycarbonyl group; the (C3–C8 cycloalkoxy)carbonyl group represented by $R^{12}$ may include cyclopropoxycarbonyl group, cyclobutoxycarbonyl group, cyclopentyloxycarbonyl group and cyclohexyloxycarbonyl group; the (C3–C6 alkenyloxy)carbonyl group represented by $R^{12}$ may include allyloxycarbonyl group; the (C3–C6 alkynyloxy)carbonyl group represented by $R^{12}$ may include propargyloxycarbonyl group; and the C1–C3 alkoxy (C1–C3 alkoxy)carbonyl group represented by $R^{12}$ may include methoxymethoxycarbonyl group, 2-methoxyethoxycarbonyl group and 2-ethoxyethoxycarbonyl group. The C1–C3 alkyl group represented by $R^{13}$ may include methyl group and ethyl group. The C1–C6 alkyl group represented by $R^{14}$ may include methyl group, ethyl group and isopropyl group; the C1–C6 haloalkyl group represented by $R^{14}$ may include chloromethyl group, bromomethyl group, fluoromethyl group, dichloromethyl group, dibromomethyl group and difluoromethyl group; the hydroxy C1–C3 alkyl group represented by $R^{14}$ may include hydroxymethyl group and 2-hydroxyethyl group; the (C1–C3 alkoxy) C1–C3 alkyl group represented by $R^{14}$ may include methoxymethyl group, ethoxymethyl group and isopropoxymethyl group; the (C1–C6 alkyl)carbonyloxy C1–C3 alkyl group represented by $R^{14}$ may include acetoxymethyl group and propionyloxymethyl group; the (C1–C6 haloalkyl)carbonyloxy C1–C3 alkyl group represented by $R^{14}$ may include trifluoroacetoxymethyl group and difluoroacetoxymethyl group; the (C1–C6 alkoxy)carbonyl group represented by $R^{14}$ may include methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group and hexyloxycarbonyl group; the (C1–C6 haloalkoxy) carbonyl group represented by $R^{14}$ may include 2,2,2-trifluoroethoxycarbonyl group, 2-fluoroethoxycarbonyl group, 2-chloroethoxycarbonyl group and 2-bromoethoxycarbonyl group; the (C3–C8 cycloalkoxy) carbonyl group represented by $R^{14}$ may include cyclopropoxycarbonyl group, cyclobutoxycarbonyl group, cyclopentyloxycarbonyl group and cyclohexyloxycarbonyl group; the (C3–C6 alkenyloxy)carbonyl group represented by $R^{14}$ may include allyloxycarbonyl group; the (C3–C6 alkynyloxy)carbonyl group represented by $R^{14}$ may include propargyloxycarbonyl group; and the C1–C3 alkoxy (C1–C3 alkoxy)carbonyl group represented by $R^{14}$ may include methoxymethoxycarbonyl group, 2-methoxyethoxycarbonyl group and 2-ethoxyethoxycarbonyl group. The C1–C6 alkyl group represented by $R^{15}$ may include methyl group, ethyl group, propyl group, isopropyl group, butyl group, isobutyl group, sec-butyl group, tert-butyl group, pentyl group and hexyl group; the C1–C6 haloalkyl group represented by $R^{15}$ may include trifluoromethyl group, difluoromethyl group, 2-fluoroethyl group, 2-chloroethyl group and 2-bromoethyl group; the C3–C8 cycloalkyl group represented by $R^{15}$ may include cyclopropyl group, cyclobutyl group, cyclopentyl group and cyclohexyl group; the (C3–C8 cycloalkyl) C1–C3 alkyl group represented by $R^{15}$ may include cyclopropylmethyl group, cyclobutylmethyl group, cyclopentylmethyl group and cyclohexylmethyl group; the C3–C6 alkenyl group represented by $R^{15}$ may include allyl group, 1-methyl-2-propenyl group, 2-methyl-2-propenyl group and 1,1-dimethyl-2-propenyl group; the C3–C6 alkynyl group represented by $R^{15}$ may include propargyl group, 1-methyl-2-propynyl group, 2-butynyl group and 1,1-dimethyl-2-propynyl group; the cyano C1–C3 alkyl group represented by $R^{15}$ may include cyanomethyl group, 1-cyanoethyl group, 2-cyanoethyl group and 1-methyl-2-cyanoethyl group; the (C1–C3 alkoxy) C1–C3 alkyl group represented by $R^{15}$ may include methoxymethyl group, 2-methoxyethyl group, ethoxymethyl group and 2-ethoxyethyl group; the (C1–C3 alkylthio) C1–C3 alkyl group represented by $R^{15}$ may include methylthiomethyl group, 2-ethylthioethyl group and 2-methylthioethyl group; the (C1–C6 alkyl) carbonyl group represented by $R^{15}$ may include acetyl group, propionyl group, butyryl group, isobutyryl group and pivaloyl group; the (C1–C6 haloalkyl)carbonyl group represented by $R^{15}$ may include trifluoroacetyl group, difluoroacetyl group, trichloroacetyl group and dichloroacetyl group; the (C3–C8 cycloalkyl)carbonyl group represented by $R^{15}$ may include cyclopropylcarbonyl group, cyclopentylcarbonyl group and cyclohexylcarbonyl group; the carboxy C1–C3 alkyl group represented by $R^{15}$ may include carboxymethyl group, 1-carboxyethyl group, 1-methyl-1-carboxyethyl group, 1-carboxypropyl group, 2-carboxyethyl group and 1-methyl-2-carboxyethyl group; the (C1–C6 alkoxy)carbonyl C1–C3 alkyl group represented by $R^{15}$ may include methoxycarbonylmethyl group, ethoxycarbonylmethyl group, propoxycarbonylmethyl group, isopropoxycarbonylmethyl group, butoxycarbonylmethyl group, isobutoxycarbonylmethyl group, sec-butoxycarbonylmethyl group, tert-butoxycarbonylmethyl group, pentyloxycarbonylmethyl group, isopentyloxycarbonylmethyl group, hexyloxycarbonylmethyl group, isohexyloxycarbonylmethyl group, 1-methoxycarbonylethyl group, 1-ethoxycarbonylethyl group, 1-(tropoxycarbonyl)ethyl group, 1-(isopropoxycarbonyl)ethyl group, 1-(butoxycarbonyl)ethyl group, 1-(isobutoxycarbonyl)ethyl group, 1-(sec-butoxycarbonyl)ethyl group, 1-(tert-butoxycarbonyl)ethyl group, 1-(pentyloxycarbonyl)ethyl group, 1-(isopentyloxycarbonyl)ethyl group, 1-(hexyloxycarbonyl)ethyl group and 1-methyl-1-(isohexyloxycarbonyl)ethyl group; the (C1–C6 haloalkoxy) carbonyl C1–C3 alkyl group represented by $R^{15}$ may include 2-fluoroethoxycarbonylmethyl group, 2-chloroethoxycarbonylmethyl group, 2-bromoethoxyearbonylmethyl group, 2,2,2-trifluoroethoxycarbonylmethyl group, 1-(2-fluoroethoxycarbonyl)ethyl group, 1-(2-chloroethoxycarbonyl)ethyl group, 1-(2-bromoethoxycarbonyl)ethyl group, 1-(2,2,2-trifluoroethoxycarbonyl)ethyl group, 1-methyl-1-(2-fluoroethoxycarbonyl)ethyl group, 1-methyl-1-(2-chloroethoxycarbonyl)ethyl group, 1-methyl-1-(2-bromoethoxycarbonyl)ethyl group and 1-methyl-1-(2,2,2-trifluoroethoxycarbonyl)ethyl group; the (C3–C8 cycloalkoxy)carbonyl C1–C3 alkyl group represented by $R^{15}$ may include cyclopropoxycarbonylmethyl group, cyclobutoxycarbonylmethyl group, cyclopentyloxycarbonylmethyl group, cyclohexyloxycarbonylmethyl group, 1-cyclopropoxycarbonylethyl group, 1-cyclobutoxycarbonylethyl group, 1-cyclopentyloxycarbonylethyl group, 1-cyclohexyloxycarbonylethyl group, 1-methyl-(1-cyclopropoxycarbonyl)ethyl group, 1-methyl-(1-cyclobutoxycarbonyl)ethyl group, 1-methyl-(1-cyclopentyloxycarbonyl)ethyl group and 1-methyl-(1-cyclohexyloxycarbonyl)ethyl group; the (C3–C6 alkenyloxy)carbonyl C1–C3 alkyl group represented by $R^{15}$ may include allyloxycarbonylmethyl group, (1-methyl-2-propenyloxy)carbonylmethyl group, 2-methyl-2-propenyloxycarbonylmethyl group, 1,1-dimethyl-2-propenyloxycarbonylmethyl group, 1-(allyloxycarbonyl)ethyl group, 1-(1-methyl-2-propenyloxycarbonyl)ethyl group, 1-(2-methyl-2-propenyloxycarbonyl)ethyl group, 1-(1,1-dimethyl-2-propenyloxycarbonyl)ethyl group, 1-methyl-1-(allyloxycarbonyl)ethyl group, 1-methyl-1-(1-methyl-2-propenyloxycarbonyl)ethyl group, 1-methyl-1-(2-methyl-2-propenyloxycarbonyl)ethyl group and 1-methyl-1-(1,1-dimethyl-2-propenyloxycarbonyl)ethyl group; the (C3–C6 alkynyloxy)carbonyl C1–C3 alkyl group represented by $R^{15}$ may include propargyloxycarbonylmethyl group, 1-methyl-2-propynyloxycarbonylmethyl group, 2-butynyloxycarbonylmethyl group, 1,1-dimethyl-2-propynyloxycarbonylmethyl group, 1-(propargyloxycarbonyl)ethyl group, 1-(1-methyl-2-propynyloxycarbonyl)ethyl group, 1-(2-butynyloxycarbonyl)ethyl group, 1-(1,1-dimethyl-2-propynyloxycarbonyl)ethyl group, 1-methyl-1-(propargyloxycarbonyl)ethyl group, 1-methyl-1-(1-methyl-2-propynyloxycarbonyl)ethyl group, 1-methyl-1-(2-butynyloxycarbonyl)ethyl group and 1-methyl-1-(1,1-dimethyl-2-propynyloxycarbonyl)ethyl group; the C1–C3 alkoxy (C1–C3 alkoxy)carbonyl C1–C3 alkyl group represented by $R^{15}$ may include methoxymethoxycarbonylmethyl group, 2-methoxyethoxycarbonylmethyl group, ethoxymethoxycarbonylmethyl group, 2-ethoxyethoxycarbonylmethyl group, 1-(methoxymethoxycarbonyl)ethyl group, 1-(2-methoxyethoxycarbonyl)ethyl group, 1-(ethoxymethoxycarbonyl)ethyl group, 1-(2-ethoxyethoxycarbonyl)ethyl group, 1-methyl-1-(methoxymethoxycarbonyl)ethyl group, 1-methyl-1-(2-methoxyethoxycarbonyl)ethyl group, 1-methyl-1-(ethoxymethoxycarbonyl)ethyl group and 1-methyl-1-(2-ethoxyethoxycarbonyl)ethyl group; the carboxy (C1–C3 alkoxy)carbonyl C1–C3 alkyl group represented by $R^{15}$ may include carboxymethoxycarbonylmethyl group, 1-(carboxy)ethoxycarbonylmethyl group, 1-(carboxymethoxycarbonyl)

ethyl group, 1-{1-(carboxy)ethoxycarbonyl}ethyl group, {1-methyl-1-(carboxy)ethoxy}carbonylmethyl group and 1-{1-methyl-1-(carboxy)ethoxycarbonyl}ethyl group; the (C1–C6 alkoxy)carbonyl (C1–C3 alkoxy)carbonyl C1–C3 alkyl group represented by $R^{15}$ may include methoxycarbonylmethoxycarbonylmethyl group, 1-(methoxycarbonyl)ethoxycarbonylmethyl group, 1-(methoxycarbonylmethoxycarbonyl)ethyl group, 1-{1-(methoxycarbonyl)ethoxycarbonyl}ethyl group, 1-methyl-1-(methoxycarbonyl)ethoxycarbonylmethyl group, 1-{1-methyl-1-(methoxycarbonyl)ethoxycarbonyl}ethyl group, ethoxycarbonylmethoxycarbonylmethyl group, 1-(ethoxycarbonyl)ethoxycarbonylmethyl group, 1-(ethoxycarbonylmethoxycarbonyl)ethyl group, 1-{1-(ethoxycarbonyl)ethoxycarbonyl}ethyl group, 1-methyl-1-(ethoxycarbonyl)ethoxycarbonylmethyl group and 1-{1-methyl-1-(ethoxycarbonyl)ethoxycarbonyl}ethyl group; the (C1–C6 haloalkoxy)carbonyl (C1–C3 alkoxy)carbonyl C1–C3 alkyl group represented by $R^{15}$ may include 2-fluoroethoxycarbonylmethoxycarbonylmethyl group, 1-(2-fluoroethoxycarbonyl)ethoxycarbonylmethyl group, 1-(2-fluoroethoxycarbonylmethoxycarbonyl)ethyl group, 1-{1-(2-fluoroethoxycarbonyl)ethoxycarbonyl}ethyl group, 1-methyl-1-(2-fluoroethoxycarbonyl)ethoxycarbonylmethyl group, 1-{1-methyl-1-(2-fluoroethoxycarbonyl)ethoxycarbonyl}ethyl group, 2-chloroethoxycarbonylmethoxycarbonylmethyl group, 1-(2-chloroethoxycarbonyl)ethoxycarbonylmethyl group, 1-(2-chloroethoxycarbonylmethoxycarbonyl)ethyl group, 1-{1-(2-chloroethoxycarbonyl)ethoxycarbonyl}ethyl group, 1-methyl-1-(2-chloroethoxycarbonyl)ethoxycarbonylmethyl group and 1-{1-methyl-1-(2-chloroethoxycarbonyl)ethoxycarbonyl}ethyl group; the (C3–C8 cycloalkoxy)carbonyl (C1–C3 alkoxy)carbonyl C1–C3 alkyl group represented by $R^{15}$ may include cyclopentyloxycarbonylmethoxycarbonylmethyl group, 1-(cyclopentyloxycarbonyl)ethoxycarbonylmethyl group, 1-(cyclopentyloxycarbonylethoxy)ethyl group, 1-{1-(cyclopentyloxycarbonyl)ethoxycarbonyl}ethyl group, 1-methyl-1-(cyclopentyloxycarbonyl)ethoxycarbonylmethyl group and 1-{1-methyl-1-(cyclopentyloxycarbonyl)ethoxycarbonyl}ethyl group; the (C13–C6 alkenyloxy)carbonyl (C1–C3 alkoxy)carbonyl C1–C3 alkyl group represented by $R^{15}$ may include allyloxycarbonylmethoxycarbonylmethyl group, 1-(allyloxycarbonyl)ethoxycarbonylmethyl group, 1-(allyloxycarbonylmethoxycarbonyl)ethyl group, 1-{1-(allyloxycarbonyl)ethoxycarbonyl}ethyl group, 1-methyl-1-(allyloxycarbonyl)ethoxycarbonylmethyl group and 1-{1-methyl-1-(allyloxycarbonyl)ethoxycarbonyl}ethyl group; the (C3–C6 alkynyloxy)carbonyl (C1–C3 alkoxy)carbonyl C1–C3 alkyl group represented by $R^{15}$ may include propargyloxycarbonylmethoxycarbonylmethyl group, 1-(propargyloxycarbonyl)ethoxycarbonylmethyl group, 1-(propargyloxycarbonylmethoxycarbonyl)ethyl group, 1-{1-(propargyloxycarbonyl)ethoxycarbonyl}ethyl group, 1-methyl-1-(propargyloxycarbonyl)ethoxycarbonylmethyl group and 1-{1-methyl-1-(propargyloxycarbonyl)ethoxycarbonyl}ethyl group; the optionally substituted aryloxycarbonyl C1–C3 alkyl group represented by $R^{15}$ may include phenoxycarbonylmethyl group, 1-phenoxycarbonylethyl group and 1-methyl-1-(phenoxycarbonyl)ethyl group; the optionally substituted aryl (C1–C3 alkoxy)carbonyl C1–C3 alkyl group represented by $R^{15}$ may include benzyloxycarbonylmethyl group, 1-benzyloxycarbonylethyl group, 1-methyl-1-(benzyloxycarbonyl)ethyl group, phenethyloxycarbonylmethyl ethyl group, 1-phenethyloxycarbonylethyl group and 1-methyl-1-(phenethyloxycarbonyl)ethyl group; and the (C1–C6 alkoxy)carbonyl group represented by $R^{15}$ may include methoxycarbonyl group, ethoxycarbonyl group, propoxycarbonyl group and isopropoxycarbonyl group. The C1–C3 alkyl group represented by $R^{17}$ may include methyl group, ethyl group, propyl group and isopropyl group; and the C1–C3 haloalkyl group represented by $R^{17}$ may include chloromethyl group and trifluoromethyl group. The C1–C3 alkyl group represented by $R^{18}$ may include methyl group and ethyl group; and the (C1–C6 alkoxy)carbonyl group represented by $R^{18}$ may include methoxycarbonyl group and ethoxycarbonyl group. The halogen atom represented by $R^{19}$ may include fluorine atom, chlorine atom, bromine atom and iodine atom. The C1–C6 alkyl group represented by $R^{19}$ may include methyl group, ethyl group, propyl group, isopropyl group, butyl group, isobutyl group, sec-butyl group, tert-butyl group, pentyl group and hexyl group; the C1–C6 haloalkyl group represented by $R^{19}$ may include trifluoromethyl group, difluoromethyl group, 2-fluoroethyl group, 2-chloroethyl group and 2-bromoethyl group; the C1–C6 alkoxy group represented by $R^{19}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{19}$ may include 2-fluoroethoxy group, 2-chloroethoxy group and 2-bromoethoxy group; the C3–C8 cycloalkoxy group represented by $R^{19}$ may include cyclopropoxy group, cyclobutoxy group, cyclopentyloxy group and cyclohexyloxy group; the C3–C6 alkenyloxy group represented by $R^{19}$ may include allyloxy group, 1-methyl-2-propenyloxy group, 2-methyl-2-propenyloxy group and 1,1-dimethyl-2-propenyloxy group; the C3–C6 alkynyloxy group represented by $R^{19}$ may include propargyloxy group, 1-methyl-2-propynyloxy group, 2-butynyloxy group and 1,1-dimethyl-2-propynyloxy group; the carboxy C1–C3 alkoxy group represented by $R^{19}$ may include carboxymethoxy group, 1-carboxyethoxy group and 1-methyl-1-(carboxy) ethoxy group; the (C1–C6 alkoxy)carbonyl C1–C3 alkoxy group represented by $R^{19}$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1-(propoxycarbonyl)ethoxy group, 1-(isopropoxycarbonyl)ethoxy group, 1-(butoxycarbonyl)ethoxy group, 1-(isobutoxycarbonyl)ethoxy group, 1-(sec-butoxycarbonyl)ethoxy group, 1-(tert-butoxycarbonyl)ethoxy group, 1-(pentyloxycarbonyl)ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxycarbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(1butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl)ethoxy group, 1-methyl-1-(isopentyloxycarbonyl)ethoxy group, 1-methyl-1-

(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^{19}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^{19}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; and the (C3–C6 alkynyloxy)carbonyl C1–C3 alkoxy group represented by $R^{19}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group. The halogen atom represented by $R^{20}$ may include fluorine atom, chlorine atom, bromine atom and iodine atom; the C1–C6 alkyl group represented by $R^{20}$ may include methyl group, ethyl group, propyl group, isopropyl group, butyl group, isobutyl group, sec-butyl group, tert-butyl group, pentyl group and hexyl group; the C1–C6 haloalkyl group represented by $R^{20}$ may include trifluoromethyl group, difluoromethyl group, 2-fluoroethyl group, 2-chloroethyl group and 2-bromoethyl group; the C1–C6 alkoxy group represented by $R^{20}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{20}$ may include 2-fluoroethoxy group, 2-chloroethoxy group and 2-bromoethoxy group; the C3–C8 cycloalkoxy group represented by $R^{20}$ may include cyclopropoxy group, cyclobutoxy group, cyclopentyloxy group and cyclohexyloxy group; the C3–C6 alkenyloxy group represented by $R^{20}$ may include allyloxy group, 1-methyl-2-propenyloxy group, 2-methyl-2-propenyloxy group and 1,1-dimethyl-2-propenyloxy group; the C3–C6 alkynyloxy group represented by $R^{20}$ may include propargyloxy group, 1-methyl-2-propynyloxy group, 2-butynyloxy group and 1,1-dimethyl-2-propynyloxy group; the carboxy C1–C3 alkoxy group represented by $R^{20}$ may include carboxymethoxy group, 1-carboxyethoxy group and 1-methyl-1-(carboxy)ethoxy group; the (C1–C6 alkoxy)carbonyl C1–C3 alkoxy group represented by $R^{20}$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1-(propoxycarbonyl)ethoxy group, 1-(isopropoxycarbonyl)ethoxy group, 1-(butoxycarbonyl)ethoxy group, 1-(isobutoxycarbonyl)ethoxy group, 1-(sec-butoxycarbonyl)ethoxy group, 1-(tert-butoxycarbonyl)ethoxy group, 1-(pentyloxycarbonyl)ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxycarbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl)ethoxy group, 1-methyl-1-(isopentyloxycarbonyl)ethoxy group, 1-methyl-1-(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^{20}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-(1-cyclopropoxycarbonyl)ethoxy group, 1-methyl-(1-cyclobutoxycarbonyl)ethoxy group, 1-methyl-(1-cyclopentyloxycarbonyl)ethoxy group and 1-methyl-(1-cyclohexyloxycarbonyl)ethoxy group; the (C3–C6 alkenyloxy)carbonyl C1–C3 alkoxy group represented by $R^{20}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; and the (C3–C6 alkynyloxy)carbonyl C1–C3 alkoxy group represented by $R^{20}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group. The C1–C3 alkyl group represented by $R^{21}$ and $R^{22}$ may include methyl group, ethyl group and propyl group; the C2–C5 alkylene group represented by $R^{21}$ and $R^{22}$ may include ethylene group, trimethylene group, tetramethylene group and pentamethylene group; and the C1–C3 alkyleneoxy C1–C3 alkylene group represented by $R^{21}$ and $R^{22}$ may include ethyleneoxyethylene group. The C1–C3 alkyl group represented by $R^{23}$ and $R^{24}$ may include methyl group, ethyl group and propyl group; the C2–C5 alkylene group represented by $R^{23}$ and $R^{24}$ may include ethylene group, trimethylene group, tetramethylene group and pentamethylene group; and the (C1–C3 alkyleneoxy) C1–C3 alkylene group represented by $R^{23}$ and $R^{24}$ may include ethyleneoxyethylene group. The C1–C3 alkyl group represented by $R^{25}$ may include methyl group and ethyl group; and the (C1–C6 alkoxy)carbonyl group represented by $R^{25}$ may include methoxycarbonyl group and ethoxycarbonyl group. The halogen atom represented by $R^{26}$ may include fluorine atom, chlorine atom, bromine atom and iodine atom; the C1–C6 alkyl group represented by $R^{26}$ may include methyl group, ethyl group, propyl group, isopropyl group, butyl group, isobutyl group, sec-butyl group, tert-butyl group, pentyl group and hexyl group; the C1–C6 haloalkyl group represented by $R^{26}$ may include trifluoromethyl group, difluoromethyl group, 2-fluoroethyl group, 2-chloroethyl group and 2-bromoethyl group; the C1–C6 alkoxy group represented by $R^{26}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{26}$ may include 2-fluoroethoxy group, 2-chloroethoxy group and 2-bromoethoxy group; the C3–C8 cycloalkoxy group represented by $R^{26}$ may include cyclopropoxy group, cyclobutoxy group, cyclopentyloxy group and cyclohexyloxy group; the C3–C6 alkenyloxy group represented by $R^{26}$ may include allyloxy group, 1-methyl-2-propenyloxy group, 2-methyl-2-propenyloxy group and 1,1-dimethyl-2-propenyloxy group; the C3–C6 alkynyloxy group represented by $R^{26}$ may include propargyloxy group, 1-methyl-2-propynyloxy group, 2-butynyloxy group and 1,1-dimethyl-2-propynyloxy group; the carboxy C1–C3 alkoxy group represented by $R^{26}$ may include carboxymethoxy group, 1-carboxyethoxy group and 1-methyl-1-(carboxy)ethoxy group; the (C1–C6 alkoxy)carbonyl C1–C3 alkoxy group represented by $R^{26}$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1-(propoxycarbonyl)ethoxy group, 1-(isopropoxycarbonyl)ethoxy group, 1-(butoxycarbonyl)ethoxy group, 1-(isobutoxycarbonyl)ethoxy group, 1-(sec-butoxycarbonyl)ethoxy group, 1-(tert-butoxycarbonyl)ethoxy group, 1-(pentyloxycarbonyl)ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxycarbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl)ethoxy group, 1-methyl-1-(isopentyloxycarbonyl)ethoxy group, 1-methyl-1-(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^{26}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^{26}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; and the (C3–C6 alkynyloxy)carbonyl C1–C3 alkoxy group represented by $R^{26}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group. The halogen atom represented by $R^{27}$ may include fluorine atom, chlorine atom, bromine atom and iodine atom; the C1–C6 alkyl group represented by $R^{27}$ may include methyl group, ethyl group, propyl group, isopropyl group, butyl group, isobutyl group, sec-butyl group, tert-butyl group, pentyl group and hexyl group; the C1–C6 haloalkyl group represented by $R^{27}$ may include trifluoromethyl group, difluoromethyl group, 2-fluoroethyl group, 2-chloroethyl group and 2-bromoethyl group; the C1–C6 alkoxy group represented by $R^{27}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{27}$ may include 2-fluoroethoxy group, 2-chloroethoxy group and 2-bromoethoxy group; the C3–C8 cycloalkoxy group represented by $R^{27}$ may include cyclopropoxy group, cyclobutoxy group, cyclopentyloxy group and cyclohexyloxy group; the C3–C6 alkenyloxy group represented by $R^{27}$ may include allyloxy group, 1-methyl-2-propenyloxy group, 2-methyl-2-propenyloxy group and 1,1-dimethyl-2-propenyloxy group; the C3–C6 alkynyloxy group represented by $R^{27}$ may include propargyloxy group, 1-methyl-2-propynyloxy group, 2-butynyloxy group and 1,1-dimethyl-2-propynyloxy group; the carboxy C1–C3 alkoxy group represented by $R^{27}$ may include carboxymethoxy group, 1-carboxyethoxy group and 1-methyl-1-(carboxy)ethoxy group; the (C1–C6 alkoxy)carbonyl C1–C3 alkoxy group represented by $R^{27}$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1 -(propoxycarbonyl) ethoxy group, 1-(isopropoxycarbonyl)ethoxy group, 1-(butoxycarbonyl)ethoxy group, 1-(isobutoxycarbonyl) ethoxy group, 1-(sec-butoxycarbonyl)ethoxy group, 1-(tert-butoxycarbonyl)ethoxy group, 1-(pentyloxycarbonyl) ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxy carbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl)ethoxy group, 1-methyl-1-(isopentyloxycarbonyl)ethoxy group, 1-methyl-1-(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^{27}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^{27}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl- 2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; and the (C3–C6 alkynyloxy)carbonyl C1–C3 alkoxy group represented by $R^{27}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2 -propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group. The C1–C6 alkyl group represented by $R^{28}$, $R^{29}$, $R^{30}$ and $R^{31}$ may include methyl group and ethyl group. The halogen atom represented by $R^{32}$, $R^{33}$ and $R^{34}$ may include fluorine atom, chlorine atom, bromine atom and iodine atom; the C1–C3 alkyl group represented by $R^{32}$, $R^{33}$ and $R^{34}$ may include methyl group, ethyl group, propyl group and isopropyl group; the C1–C3 haloalkyl group represented by $R^{32}$, $R^{33}$ and $R^{34}$ may include trifluoromethyl group, difluoromethyl group, fluoromethyl group, chloromethyl group and bromomethyl group; the (C1–C6 alkoxy)carbonyl group represented by $R^{32}$, $R^{33}$ and $R^{34}$ may include methoxycarbonyl group, ethoxycarbonyl group, propoxycarbonyl group and isopropoxycarbonyl group; the (C3–C8 cycloalkoxy)carbonyl group represented by $R^{32}$, $R^{33}$ and $R^{34}$ may include cyclopropoxycarbonyl group, cyclobutoxycarbonyl group, cyclopentyloxycarbonyl group and cycloheyloxycarbonyl group; the (C3–C6 alkenyloxy)carbonyl group represented by $R^{32}$, $R^{33}$ and $R^{34}$ may include allyloxycarbonyl group, 1-methyl-2-propenyloxycarbonyl group and 2-methyl-2-propenyloxycarbonyl group; the (C3–C6 alkynyloxy) carbonyl group represented by $R^{32}$, $R^{33}$ and $R^{34}$ may include propargyloxycarbonyl group, 1-methyl-2-propynyloxycarbonyl group and 2-butynyloxycarbonyl group; the carboxy C1–C3 alkyl group represented by $R^{32}$, $R^{33}$ and $R^{34}$ may include carboxymethyl group, 1-carboxyethyl group and 1-methyl-1-(carboxy)ethyl group; the (C1–C6 alkoxy)carbonyl C1–C3 alkyl group represented by $R^{32}$, $R^{33}$ and $R^{34}$ may include methoxycarbonylmethyl group, ethoxycarbonylmethyl group, propoxycarbonylmethyl group, isopropoxycarbonylmethyl group, butoxycarbonylmethyl group, isobutoxycarbonylmethyl group, sec-butoxycarbonylmethyl group, tert-butoxycarbonylmethyl group, pentyloxycarbonylmethyl group, isopentyloxycarbonylmethyl group, hexyloxycarbonylmethyl group, isohexyloxycarbonylmethyl group, 1-methoxycarbonylethyl group, 1-ethoxycarbonylethyl group, 1-(propoxycarbonyl)ethyl group, 1-(isopropoxycarbonyl)ethyl group, 1-(butoxycarbonyl)ethyl group, 1-(isobutoxycarbonyl)ethyl group, 1-(sec-butoxycarbonyl)ethyl group, 1-(tert-butoxycarbonyl)ethyl group, 1-(pentyloxycarbonyl)ethyl group, 1-(isopentyloxycarbonyl)ethyl group, 1-(hexyloxycarbonyl)ethyl group, 1-(isohexyloxycarbonyl)ethyl group, 1-methyl-1-(methoxycarbonyl)ethyl group, 1-methyl-1-(ethoxycarbonyl)ethyl group, 1-methyl-1-(propoxycarbonyl)ethyl group, 1-methyl-1-(isopropoxycarbonyl)ethyl group, 1-methyl-1-(butoxycarbonyl)ethyl group, 1-methyl-1-(isobutoxycarbonyl)ethyl group, 1-methyl-1-(sec-butoxycarbonyl)ethyl group, 1-methyl-1-(tert-butoxycarbonyl)ethyl group, 1-methyl-1-(pentyloxycarbonyl)ethyl group, 1-methyl-1-(isopentyloxycarbonyl)ethyl group, 1-methyl-1-(hexyloxycarbonyl)ethyl group and 1-methyl-1-(isohexyloxycarbonyl)ethyl group; the (C3–C8 cycloalkoxy)carbonyl C1–C3 alkyl group represented by $R^{32}$, $R^{33}$ and $R^{34}$ may include cyclopropoxycarbonylmethyl group, cyclobutoxycarbonylmethyl group, cyclopentyloxycarbonylmethyl group, cyclohexyloxycarbonylmethyl group, 1-cyclopropoxycarbonylethyl group, 1-cyclobutoxycarbonylethyl group, 1-cyclopentyloxycarbonylethyl group, 1-cyclohexyloxycarbonylethyl group, 1-methyl-1-(cyclopropoxycarbonyl)ethyl group, 1-methyl-1-

(cyclobutoxycarbonyl)ethyl group, 1-methyl-1-(cyclopentyloxycarbonyl)ethyl group and 1-methyl-1-(cyclohexyloxycarbonyl)ethyl group; the (C3–C6 alkenyloxy)carbonyl C1–C3 alkyl group represented by $R^{32}$, $R^{33}$ and $R^{34}$ may include allyloxycarbonylmethyl group, 1-methyl-2-propenyloxycarbonylmethyl group, 2-methyl-2-propenyloxycarbonylmethyl group, 1,1-dimethyl-2-propenyloxycarbonylmethyl group, 1-(allyloxycarbonyl)ethyl group, 1-(1-methyl-2-propenyloxycarbonyl)ethyl group, 1-(2-methyl-2-propenyloxycarbonyl)ethyl group, 1-(1,1-dimethyl-2-propenyloxycarbonyl)ethyl group, 1-methyl-1-(allyloxycarbonyl)ethyl group, 1-methyl-1-(1-methyl-2-propenyloxycarbonyl)ethyl group, 1-methyl-1-(2-methyl-2-propenyloxycarbonyl)ethyl group and 1-methyl-1-(1,1-dimethyl-2-propenyloxycarbonyl)ethyl group; the (C3–C6 alkynyloxy) carbonyl C1- C3 alkyl group represented by $R^{32}$, $R^{33}$ and $R^{34}$ may include propargyloxycarbonylmethyl group, 1-methyl-2-propynyloxycarbonylethyl group, 2-butynyloxycarbonylmethyl group, 1,1-dimethyl-2-propynyloxycarbonylmethyl group, 1-(propargyloxycarbonyl)ethyl group, 1-(1-methyl-2-propynyloxycarbonyl) ethyl group, 1-(2-butynyloxycarbonyl)ethyl group, 1-(1,1-dimethyl-2-propynyloxycarbonyl)ethyl group, 1-methyl-1-(propargyloxycarbonyl)ethyl group, 1-methyl-1-(1-methyl-2-propynyloxycarbonyl)ethyl group, 1-methyl-1-(2-butynyloxycarbonyl)ethyl group and 1-methyl-1-(1,1-dimethyl-2-propynyloxycarbonyl)ethyl group; the carboxy C1–C3 alkoxy group represented by $R^{32}$, $R^{33}$ and $R^{34}$ may include carboxymethoxy group, 1-carboxyethoxy group and 1-methyl-1-(carboxy)ethoxy group; the (C1–C6 alkoxy)carbonyl C1–C3 alkoxy group represented by $R^{32}$, $R^{33}$ and $R^{34}$ may include methoxycarboxymethoxy group, ethoxycarboxymethoxy group, propoxycarboxymethoxy group, isopropoxycarboxymethoxy group, butoxycarboxymethoxy group, isobutoxycarboxymethoxy group, sec-butoxycarboxymethoxy group, tert-butoxycarboxymethoxy group, pentyloxycarboxymethoxy group, isopentyloxycarboxymethoxy group, hexyloxycarboxymethoxy group, isohexyloxycarboxymethoxy group, 1-methoxycarboxyethoxy group, 1-ethoxycarboxyethoxy group, 1-(propoxycarboxy)ethoxy group, 1-(isopropoxycarboxy)ethoxy group, 1-(butoxycarboxy)ethoxy group, 1-(isobutoxycarboxy)ethoxy group, 1-(sec-butoxycarboxy)ethoxy group, 1-(tert-butoxycarboxy)ethoxy group, 1-(pentyloxycarboxy)ethoxy group, 1-(isopentyloxycarboxy)ethoxy group, 1-(hexyloxycarboxy)ethoxy group, 1-(isohexyloxycarboxy)ethoxy group, 1-methyl-1-(methoxycarboxy)ethoxy group, 1-methyl-1-(ethoxycarboxy)ethoxy group, 1-methyl-1-(propoxycarboxy)ethoxy group, 1-methyl-1-(isopropoxycarboxy)ethoxy group, 1-methyl-1-(butoxycarboxy)ethoxy group, 1-methyl-1-(isobutoxycarboxy)ethoxy group, 1-methyl-1-(sec-butoxycarboxy)ethoxy group, 1-methyl-1-(tert-butoxycarboxy)ethoxy group, 1-methyl-1-(pentyloxycarboxy)ethoxy group, 1-methyl-1-(isopentyloxycarboxy)ethoxy group, 1-methyl-1-(hexyloxycarboxy)ethoxy group and 1-methyl-1-(isohexyloxycarboxy)ethoxy group; the (C3–C8 cycloalkoxy)carbonyl C1–C3 alkoxy group represented by $R^{32}$, $R^{33}$ and $R^{34}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^{32}$, $R^{33}$ and $R^{34}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; the (C3–C6 alkynyloxy)carbonyl C1–C3 alkoxy group represented by $R^{32}$, $R^{33}$ and $R^{34}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group; the carboxyl C1–C3 alkylthio group represented by $R^{32}$, $R^{33}$ and $R^{34}$ may include carboxymethylthio group, 1-carboxyethylthio group and 1-methyl-1-(carboxy)ethylthio group; the (C1–C6 alkoxy)carbonyl C1–C3 alkylthio group represented by $R^{32}$, $R^{33}$ and $R^{34}$ may include methoxycarbonylmethylthio group, ethoxycarbonylmethylthio group, propoxycarbonylmethylthio group, isopropoxycarbonylmethylthio group, butoxycarbonylmethylthio group, isobutoxycarbonylmethylthiogroup, sec-butoxycarbonylmethylthio group, tert-butoxycarbonylmethylthio group, pentyloxycarbonylmethylthio group, isopentyloxycarbonylmethylthio group, hexyloxycarbonylmethylthio group, isohexyloxycarbonylmethylthio group, 1-methoxycarbonylethylthio group, 1-ethoxycarbonylethylthio group, 1-(propoxycarbonyl)ethylthio group, 1-(isopropoxycarbonyl)ethylthio group, 1-(butoxycarbonyl)ethylthio group, 1-(isobutoxycarbonyl)ethylthio group, 1-(sec-butoxycarbonyl)ethylthio group, 1-(tert-butoxycarbonyl)ethylthio group, 1-(pentyloxycarbonyl)ethylthio group, 1-(isopentyloxycarbonyl)ethylthio group, 1-(hexyloxycarbonyl)ethylthio group, 1-(isohexyloxycarbonyl)ethylthio group, 1-methyl-1-(methoxycarbonyl)ethylthio group, 1-methyl-1-(ethoxycarbonyl)ethylthio group, 1-methyl-1-(propoxycarbonyl)ethylthio group, 1-methyl-1-(isopropoxycarbonyl)ethylthio group, 1-methyl-1-(butoxycarbonyl)ethylthio group, 1-methyl-1-(isobutoxycarbonyl)ethylthio group, 1-methyl-1-(sec-butoxycarbonyl)ethylthio group, 1-methyl-1-(tert-butoxycarbonyl)ethylthio group, 1-methyl-1-(pentyloxycarbonyl)ethylthio group, 1-methyl-1-(isopentyloxycarbonyl)ethylthio group, 1-methyl-1-(hexyloxycarbonyl)ethylthio group and 1-methyl-1-(isohexyloxycarbonyl)ethylthio group; the (C3–C8 cycloalkoxy)carbonyl C1–C3 alkylthio group represented by $R^{32}$, $R^{33}$ and $R^{34}$ may include cyclopropoxycarbonylmethylthio group, cyclobutoxycarbonylmethylthio group, cyclopentyloxycarbonylmethylthio group, cyclohexyloxycarbonylmethylthio group, 1-cyclopropoxycarbonylethylthio group, 1-cyclobutoxycarbonylethylthio group, 1-cyclopentyloxycarbonylethylthio group, 1-cyclohexyloxycarbonylethylthio group, 1-methyl-1-(cyclopropoxycarbonyl)ethylthio group, 1-methyl-1-(cyclobutoxycarbonyl)ethylthio group, 1-methyl-1-(cyclopentyloxycarbonyl)ethylthio group and 1-methyl-1-(cyclohexyloxycarbonyl)ethylthio group; the (C3–C6 alkenyloxy)carbonyl C1–C3 alkylthio group represented by $R^{32}$, $R^{33}$ and $R^{34}$ may include allyloxycarbonylmethylthio group, 1-methyl-2-propenyloxycarbonylmethylthio group, 2-methyl-2-propenyloxycarbonylmethylthio group, 1,1-dimethyl-2-propenyloxycarbonylmethylthio group, 1-(allyloxycarbonyl)ethylthio group, 1-(1-methyl-2-propenyloxycarbonyl)ethylthio group, 1-(2-methyl-2-propenyloxycarbonyl)ethylthio group, 1-(1,1-dimethyl-2-propenyloxycarbonyl)ethylthio group, 1-methyl-1-(allyloxycarbonyl)ethylthio group, 1-methyl-1-(1-methyl-2-propenyloxycarbonyl)ethylthio group, 1-methyl-1-(2-methyl-2-propenyloxycarbonyl)ethylthio group and 1-methyl-1-(1,1-dimethyl-2-propenyloxycarbonyl)ethylthio group; the (C3–C6 alkynyloxy)carbonyl C1–C3 alkylthio group represented by $R^{32}$, $R^{33}$ and $R^{34}$ may include propargyloxycarbonylmethylthio group, 1-methyl-2-propynyloxycarbonylmethylthio group, 2-butynyloxycarbonylmethylthio group, 1,1-dimethyl-2-propynyloxycarbonylmethylthio group, 1-(propargyloxycarbonyl)ethylthio group, 1-(1-methyl-2-propynyloxycarbonyl)ethylthio group, 1-(2-butynyloxycarbonyl)ethylthio group, 1-(1,1-dimethyl-2-propynyloxycarbonyl)ethylthio group, 1-methyl-1-(propargyloxycarbonyl)ethylthio group, 1-methyl-1-(1-methyl-2-propynyloxycarbonyl)ethylthio group, 1-methyl-1-(2-butynyloxycarbonyl)ethylthio group and 1-methyl-1-(1,1-dimethyl-2-propynyloxycarbonyl)ethylthio group; the carboxyl C1–C3 alkylamino group represented by $R^{32}$, $R^{33}$ and $R^{34}$ may include carboxymethylamino group, 1-carboxyethylamino group and 1-methyl-1-(carboxy)ethylamino group; the (C1–C6 alkoxy)carbonyl C1–C3 alkylamino group represented by $R^{32}$, $R^{33}$ and $R^{34}$ may include methoxycarbonylmethylamino group, ethoxycarbonylmethylamino group, propoxycarbonylmethylamino group, isopropoxycarbonylmethylamino group, butoxycarbonylmethylamino group, isobutoxycarbonylmethylamino group, sec-butoxycarbonylmethylamino group, tert-butoxycarbonylmethylamino group, pentyloxycarbonylmethylamino group, isopentyloxycarbonylmethylamino group, hexyloxycarbonylmethylamino group, isohexyloxycarbonylmethylamino group, 1-methoxycarbonylethylamino group, 1-ethoxycarbonylethylamino group, 1-(propoxycarbonyl)ethylamino group, 1-(isopropoxycarbonyl)ethylamino group, 1-(butoxycarbonyl)ethylamino group, 1-(isobutoxycarbonyl)ethylamino group, 1-(sec-butoxycarbonyl)ethylamino group, 1-(tert-butoxycarbonyl)ethylamino group, 1-(pentyloxycarbonyl)ethylamino group, 1-(isopentyloxycarbonyl)ethylamino group, 1-(hexyloxycarbonyl)ethylamino group, 1-(isohexyloxycarbonyl)ethylamino group, 1-methyl-1-(methoxycarbonyl)ethylamino group, 1-methyl-1-(ethoxycarbonyl)ethylamino group, 1-methyl-1-(propoxycarbonyl)ethylamino group, 1-methyl-1-(isopropoxycarbonyl)ethylamino group, 1-methyl-1-(butoxycarbonyl)ethylamino group, 1-methyl-1-(isobutoxycarbonyl)ethylamino group, 1-methyl-1-(sec-butoxycarbonyl)ethylamino group, 1-methyl-1-(tert-butoxycarbonyl)ethylamino group, 1-methyl-1-(pentyloxycarbonyl)ethylamino group, 1-methyl-1-(isopentyloxycarbonyl)ethylamino group, 1-methyl-1-(hexyloxycarbonyl)ethylamino group and 1-methyl-1-(isohexyloxycarbonyl)ethylamino group; the (C3–C8 cycloalkoxy)carbonyl C1–C3 alkylamino group represented by $R^{32}$, $R^{33}$ and $R^{34}$ may include cyclopropoxycarbonylmethylamino group, cyclobutoxycarbonylmethylamino group, cyclopentyloxycarbonylmethylamino group, cyclohexyloxycarbonylmethylamino group, 1-cyclopropoxycarbonylethylamino group, 1-cyclobutoxycarbonylethylamino group, 1-cyclopentyloxycarbonylethylamino group, 1-cyclohexyloxycarbonylethylamino group, 1-methyl-1-(cyclopropoxycarbonyl)ethylamino group, 1-methyl-1-(cyclobutoxycarbonyl)ethylamino group, 1-methyl-1-(cyclopentyloxycarbonyl)ethylamino group and 1-methyl-1-(cyclohexyloxycarbonyl)ethylamino group; the (C3–C6 alkenyloxy)carbonyl C1–C3 alkylamino group represented by $R^{32}$, $R^{33}$ and $R^{34}$ may include allyloxycarbonylmethylamino group, 1-methyl-2-propenyloxycarbonylmethylamino group, 2-methyl-2-propenyloxycarbonylmethylamino group, 1,1-dimethyl-2-propenyloxycarbonylmethylamino group, 1-(allyloxycarbonyl)ethylamino group, 1-(1-methyl-2-propenyloxycarbonyl)ethylamino group, 1-(2-methyl-2-propenyloxycarbonyl)ethylamino group, 1-(1,1-dimethyl-2-propenyloxycarbonyl)ethylamino group, 1-methyl-1-(allyloxycarbonyl)ethylamino group, 1-methyl-1-(1-methyl-2-propenyloxycarbonyl)ethylamino group, 1-methyl-1-(2-methyl-2-propenyloxycarbonyl)ethylamino group and 1-methyl-1-(1,1-dimethyl-2-propenyloxycarbonyl)ethylamino group; the (C3–C6 alkynyloxy)carbonyl C1–C3 alkylamino group represented by $R^{32}$, $R^{33}$ and $R^{34}$ may include propargyloxycarbonylmethylamino group, 1-methyl-2-propynyloxycarbonylmethylamino group, 2-butynyloxycarbonylmethylamino group, 1,1-dimethyl-2-propynyloxycarbonylmethylamino group, 1-(propargyloxycarbonyl)ethylamino group, 1-(1-methyl-2-propynyloxycarbonyl)ethylamino group, 1-(2-butynyloxycarbonyl)ethylamino group, 1-(1,1-dimethyl-2-propynyloxycarbonyl)ethylamino group, 1-methyl-1-(propargyloxycarbonyl)ethylamino group, 1-methyl-1-(1-methyl-2-propynyloxycarbonyl)ethylamino group, 1-methyl-1-(2-butynyloxycarbonyl)ethylamino group and 1-methyl-1-(1,1-dimethyl-2-propynyloxycarbonyl)ethylamino group; the C1–C6 alkoxy group represented by $R^{32}$, $R^{33}$ and $R^{34}$ may include methoxy group, ethoxy group and isopropoxy group; the C3–C6 alkenyloxy group represented by $R^{32}$, $R^{33}$ and $R^{34}$ may include allyl group; the C3–C6 alkynyloxy group represented by $R^{32}$, $R^{33}$ and $R^{34}$ may include propargyl group; the (C1–C6 alkyl)carbonyloxy group represented by $R^{32}$, $R^{33}$ and $R^{34}$ may include acetoxy group; the (C1–C6 alkoxy)carbonyloxy group represented by $R^{32}$, $R^{33}$ and $R^{34}$ may include methoxycarbonyloxy group and ethoxycarbonyloxy group; the C1–C6 alkylthio group represented by $R^{32}$, $R^{33}$ and $R^{34}$ may include methylthio group, ethylthio group and isopropylthio group; the C3–C6 alkenylthio group represented by $R^{32}$, $R^{33}$ and $R^{34}$ may include allylthio group; the C3–C6 alkynylthio group represented by $R^{32}$, $R^{33}$ and $R^{34}$ may include propargylthio group; the (C1–C6 alkyl)carbonylthio group represented by $R^{32}$, $R^{33}$ and $R^{34}$ may include acetylthio group; the (C1-C6 alkoxy)carbonylthio group represented by $R^{32}$, $R^{33}$ and $R^{34}$ may include methoxycarbonylthio group; the C1–C6 alkylamino group represented by $R^{32}$, $R^{33}$ and $R^{34}$ may include methylamino group and ethylamino group; the C3–C6 alkenylamino group represented by $R^{32}$, $R^{33}$ and $R^{34}$ may include allylamino group; the C3–C6 alkynylamino group represented by $R^{32}$, $R^{33}$ and $R^{34}$ may include propargylamino group; the (C1–C6 alkyl)carbonylamino group represented by $R^{32}$, $R^{33}$ and $R^{34}$ may include acetamino group; and the (C1–C6 alkoxy)carbonylamino group represented by $R^{32}$, $R^{33}$ and $R^{34}$ may include methoxycarbonylamino group and ethoxycarbonylamino group.

The typical examples of the present compound are the compounds given by the formula [I], wherein Q is a group given by Q5, Z is oxygen atom or sulfur atom, $R^1$ is trifluoromethyl group, $R^3$ is fluorine atom and $R^4$ is chlorine atom and $R^6$ is C1–C6 alkyl group, C3–C8 cycloalkyl group, C3–C6 alkenyl group or C3–C6 alkynyl group or (C1–C6 alkoxy)carbonyl C1-C3 alkyl group; wherein Q is a group given by Q6, $R^1$ is trifluoromethyl group, $R^3$ is fluorine atom and $R^4$ is chlorine atom and $R^7$ is C1–C6 alkoxy group; wherein Q is a group given by Q1, Z is sulfur atom, T is direct bond, $R^1$ is trifluoromethyl group, $R^3$ is fluorine atom and $R^{15}$ is C1–C6 alkyl group, C3–C8 cycloalkyl group, C3–C6 alkenyl group or C3–C6 alkynyl group; and wherein Q is a group given by Q1, Z is oxygen atom, T is methylene group, $R^1$ is trifluoromethyl group, $R^3$ is fluorine atom and $R^{15}$ is C1–C6 alkyl group, C3–C8 cycloalkyl group, C3–C6 alkenyl group or C3–C6 alkynyl group. The specific examples of the present compound are the compounds given by the formula [I], wherein Q is a group given by Q5, Z is oxygen atom, $R^1$ is trifluoromethyl group, $R^3$ is fluorine atom and $R^4$ is chlorine atom and $R^6$ is 1-ethoxycarbonylethyl group; wherein Q is a group given by Q5, Z is oxygen atom, $R^1$ is trifluoromethyl group, $R^3$ is fluorine atom and $R^4$ is chlorine atom and $R^6$ is ethoxycarbonyl group; wherein Q is a group given by Q5, Z is sulfur atom, $R^1$ is trifluoromethyl group, $R^3$ is fluorine atom and $R^4$ is chlorine atom and $R^6$ is methoxycarbonylmethyl group; wherein Q is a group given by Q6, $R^1$ is trifluoromethyl group, $R^3$ is fluorine atom and $R^4$ is chlorine atom and $R^7$ is isopropoxy group; wherein Q is a group given by Q5, Z is oxygen atom, $R^1$ is trifluoromethyl group, $R^3$ is fluorine atom and $R^4$ is chlorine atom and $R^6$ is 1-methoxycarbonylethyl group; wherein Q is a group given by Q1, Z is sulfur atom, T is direct bond, $R^1$ is trifluoromethyl group, $R^3$ is fluorine atom and $R^{15}$ is isopropyl group; wherein Q is a group given by Q5, Z is oxygen atom, $R^1$ is trifluoromethyl group, $R^3$ is fluorine atom and $R^4$ is chlorine atom and $R^6$ is propargyl group; and wherein Q is a group given by Q1, Z is oxygen atom, T is methylene group, $R^1$ is trifluoromethyl group, $R^3$ is fluorine atom and $R^{15}$ is propargyl group.

For the present compounds, there exist optical isomers based on the presence of asymmetric carbon atom, and all of these optical isomers and mixtures thereof are included within the scope of the present invention.

In the present compounds, preferable substituents for herbicidal effect are exemplified by trifluoromethyl group as $R^1$ and a group given by general formula Q1 as Q. Examples of preferable substituents for Q1 include hydrogen atom and fluorine atom as $R^3$, oxygen atom and sulfur atom as Z, and propargyl group and allyl group as $R^{15}$.

The process for producing the present compounds is explained in detail below.

The present compounds can be produced by the production process below:

The production process by allowing the amide compound given by the formula [II]

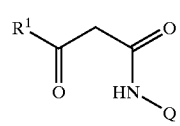

wherein $R^1$ and Q have the same meanings mentioned above, to react with a cyanate salt in the presence of a protonic acid.

In the present invention, the cyanate salt includes not only cyanate salts of the narrow meaning but also isocyanate salts. Such cyanate salts of the narrow meaning are exemplified by alkali cyanates (e.g., sodium cyanate, potassium cyanate and so on). Examples of the isocyanate salt include silver isocyanate and so on.

The reaction temperature is in the range of –20° C. to 50° C., preferably 10° C. to 45° C.

The amount of the reagents to be used is usually 1 to 10 mols, preferably 1 to 2 mols of the cyanate salt based on 1 mol of the amide compound given by the formula [II]. The amount of the protonic acid is usually 1 mol to a large excess amount, preferably 1 to 10 mols based on 1 mol of the cyanate salt.

Examples of the protonic acid include aliphatic carboxylic acids such as acetic acid, propionic acid and butyric acid; aromatic carboxylic acids such as benzoic acid and 4-nitrobenzoic acid; sulfonic acids such as p-toluenesulfonic acid and methanesulfonic acid; and inorganic acids such as hydrochloric acid and sulfuric acid.

In the present reaction, solvents, which are inert in the present reaction condition, may be used. Examples of the solvent include aliphatic hydrocarbons such as pentane, hexane, heptane, cyclopentane and cyclohexane; halogenated aliphatic hydrocarbons such as dichloromethane, chloroform and 1,2-dichloroethane; aromatic hydrocarbons such as benzene, toluene and xylene; halogenated aromatic hydrocarbons such as chlorobenzene and m-dichlorobenzene; ketones such as acetone, methyl ethyl ketone, methyl isobutyl ketone, cyclopentanone and cyclohexanone; ethers such as diethyl ether, tert-butyl methyl ether, diethylene glycol dimethyl ether, 1,4-dioxane and tetrahydrofuran; alcohols such as methanol, ethanol, 2-propanol and propanol; amides such as N,N-dimethylformamide and N,N-dimethylacetamide; sulfur-containing compounds such as dimethyl sulfoxide and sulfolane; nitro compounds such as nitromethane, nitroethane and 2-nitropropane; aliphatic nitriles such as acetonitrile; and mixtures thereof.

After completion of the reaction, the reaction mixture is usually poured into water and optionally neutralized. Thereafter, precipitated crystals are collected by filtration, or the reaction mixture is extracted with an organic solvent, dried and concentrated to give the objective compound. The compound can be purified by a technique such as recrystallization, column chromatography or the like.

Further, in the present process, it is also possible to allow the amide compound given by the formula [II] to react with cyanic acid in an inert solvent in place of allowing the amide compound given by formula [II] to react with a cyanate salt in the presence of a protonic acid. Cyanic acid can be obtained by the method described in J. Org. Chem., 28, p. 586 (1963) or the method allowing alkali metal cyanate to react with a protonic acid.

The amide compound given by the formula [II] can be prepared by the following process:

The production process by allowing an aniline compound given by the formula [III]:

wherein Q has the same meaning defined above, to react with an acetate ester compound given by the formula [IV]:

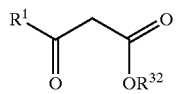

wherein $R^1$ has the same meaning defined above and $R^{32}$ represents methyl group or ethyl group, in a solvent or without solvent.

The reaction temperature in said process is usually in the range of room temperature to 150° C., or room temperature to boiling point of a solvent when the solvent is utilized. Further, by-produced alcohol (methanol or ethanol) may be distilled away from the reaction mixture or a small amount of an acid or a base may be added for the purpose of speeding up the reaction.

The amount of the acetate ester compound given by the formula [IV] is usually at the rate of 1 to 5 mols based on 1 mol of the aniline compound given by the formula [III].

Examples of the acid used for speeding up the reaction include protonic acids such as p-toluenesulfonic acid and methanesulfonic acid, and the used amount is at the rate of 0.05 to 1 mol based on 1 mol of the aniline compound given by the formula [III]. Examples of the base include tertiary amines such as triethylamine, tributylamine and N,N-dimethylaniline; pyridines such as pyridine and picoline; and inorganic bases such as potassium carbonate and sodium hydride, and the used amount is at the rate of 0.05 to 1 mol based on 1 mol of the aniline compound given by the formula [III].

Examples of the solvent include aliphatic hydrocarbons such as pentane, hexane, heptane, cyclopentane and cyclohexane; halogenated aliphatic hydrocarbons such as dichloromethane, chloroform and 1,2-dichloroethane; aromatic hydrocarbons such as benzene, toluene and xylene; halogenated aromatic hydrocarbons such as chlorobenzene and m-dichlorobenzene; ketones such as acetone, methyl ethyl ketone, methyl isobutyl ketone, cyclopentanone and cyclohexanone; ethers such as diethyl ether, tert-butyl methyl ether, diethylene glycol dimethyl ether, 1,4-dioxane and tetrahydrofuran; amides such as N,N-dimethylformamide and N,N-dimethylacetamide: sulfur-containing compounds such as dimethyl sulfoxide and sulfolane; nitro compounds such as nitromethane, nitroethane and 2-nitropropane; aliphatic nitriles such as acetonitrile; and mixtures thereof.

After the rection is ended, usual work-up procedures described below can give the objective compound.
(1) To concentrate the reaction solution directly, wash it with water and/or an organic solvent and dry it.
(2) To pour the reaction solution into water, neutralize with aqueous saturated sodium bicarbonate and the like, extract with an organic solvent, dry and concentrate it.
(3) To pour the reaction solution into water, collect precipitated crystals by filtration and dry them.

The compound may be purified by procedures such as recrystallization, column chromatography and so on.

The aniline compounds given by the formula [III] are known in Japanese laid-open patent publication Nos. Sho62-221677, Sho62-158280 and so on, and can be produced according to the procedures described therein.

The process for preparing the amide compound given by the formula [II] may give a hydrate compound of the amide compound given by the formula [II] or a mixture thereof. However, the hydrate compound can be utilized for producing the present compound by the same way as the amide compound given by the formula [II]. The hydrate compound may have the chemical structure as follows:

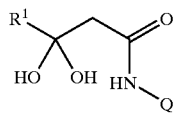

wherein $R^1$ and Q have the same meanings as defined above.

The present compounds have excellent herbicidal activity and some of them exhibit excellent selectivity between crops and weeds. Namely, the present compounds have herbicidal activity against various troublesome weeds listed below by foliar treatment or soil treatment in upland fields.

Eveningprimroses (Onagraceous weeds) such as *Oenothera erythrosepala* and *Oenothera laciniata*;

Buttercups (Ranunculaceous weeds) such as *Ranunculus muricatus* and *Ranunculus sardous*;

Docks (Polygonaceous weeds) such as wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broadleaf dock (*Rumex obtusifolius*) and Japanese knotweed (*Polygonum cuspidatum*);

Purslanes (Portulacaceous weeds) such as common purslane (*Portulaca oleracea*);

Pinks (Caryophyllaceous weeds) such as common chickweed (*Stellaria media*) and sticky chickweed (*Cerastium glomeratum*);

Goosefoots (Chenopodiaceous weeds) such as common lambsquarters (*Chenopodium album*) and kochia (*Kochia scoparia*);

Amaranths (Amaranthaceous weeds) such as redroot pigweed (*Amaranth us retroflexus*) and smooth pigweed (*Amaranthus hybridus*);

Crusifers (Cruciferous weeds) such as wild radish (*Raphanus raphanistrum*), wild mustard (*Sinapis arvensis*), shepherdpurse (*Capsella bursa-pastoris*) and *Lepidium virginicum*;

Beans (Leguminous weeds) such as hemp sesbania (*Sesbania exaltata*), sicklepod (*Cassia obtusifolia*), Florida beggarweed (*Desmodium tortuosum*), white clover (*Trifolium repens*), common vetch (*Vicia sativa*) and black medick (*Medicago lupulina*);

Mallows (Malvaceous weeds) such as velvetleaf (*Abutilon theophrasti*) and prickly sida (*Sida spinosa*);

Violets (Violaceous weeds) such as field pansy (*Viola arvensis*) and wild pansy (*Viola tricolor*);

Bedstraws (*Rubiaceous weeds*) such as catchweed bedstraw (cleavers) (*Galium aparine*);

Bindweeds (Convolvulaceous weeds) such as ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*) and field bindweed (*Convolvulus arvensis*);

Mints (Labiate weeds) such as red deadnettle (*Lamium purpureum*) and henbit (*Lamium amplexicaule*);

Nightshades (Solanaceous weeds) such as jimsonweed (*Datura stramonium*) and black nightshade (*Solanum nigrum*);

Figworts (Scrophulariaceous weeds) such as birdseye speedwell (*Veronica persica*), *Veronica arvensis* and ivyleaf speedwell (*Veronica hederaefolia*);

Composites (Composite weeds) such as common cocklebur (*Xanthium pensylvanicum*), common sunflower (*Helianthus annuus*), *Matricaria chamomilla*, scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*) and *Taraxacum officinale* Borages (Boraginaceous weeds) such as forget-me-not (*Myosotis arvensis*);

Milkweeds (Asclepiadaceous weeds) such as common milkweed (*Asclepias syriaca*);

Spurges (Euphorbiaceous weeds) such as sun spurge (*Euphorbia helioscopia*) and spotted spurge (*Euphorbia maculata*);

Geraniums (Geramiaceous weeds) such as carolina geranium (*Geranium carolinianum*);

Woodsorrels (Oxalidaceous weeds) such as *Oxalis corymbosa*; Cucurbitaceous weeds such as *Sicyos angulatus*; Grasses (Graminaceous weeds) such as barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oats (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*) and water foxtail (*Alopecurus geniculatus*);

Spiderworts (Commelinaceous weeds) such as common dayflower (*Commelina communis*);

Horsetails (Equisetaceous weeds) such as field horsetail (*Equisetum arvense*);

Sedges (Cyperaceous weeds) such as rice flatsedge (*Cyperus iria*), purple nutsedge (*Cyperus rotundus*) and yellow nutsedge (*Cyperus esculentus*).

Furthermore, some of the present compounds exhibit no significant phytotoxicity on the main crops such as corn (*Zea mays*), wheat (*Triticum aestivum*), barley (*Hordeum vulgare*), rice (*Oryza sativa*), sorghum (*Sorghum bicoloi*), soybean (*Glycine max*), cotton (*Gossypium spp.*), sugar beet (*Beta vulgaris*), peanut (*Arachis hypogaea*), sunflower (*Helianthus annuus*), and canola (*Brassica napus*); horticultural crops such as flowers and ornamental plants; and vegetable crops. The present compounds can also attain the effective control of various weeds which may cause some trouble in the no-tillage cultivation of soybean, corn, wheat and other crops. Furthermore, some of the present compounds exhibit no significant phytotoxicity on the crops.

The present compounds also have herbicidal activity against various weeds which may cause some trouble in the flooding treatment on paddy fields, such as listed below.

Grasses (Graminaceous weeds) such as barnyardgrass (*Echinochloa oryzicola*);

Figworts (Scrophulariaceous weeds) such as common falsepimpernel (*Lindernia procumbens*);

Loothsterife (Lythraceous weeds) such as Indian toothcup (*Rotala indica*), red stem (*Ammannia multiflora*);

Waterworts (Elatinaceous weeds) such as waterwort (*Elatine triandra*); Sedges (Cyperaceous weeds) such as smallflower umbrella sedge (*Cyperus difformis*), hardstem bulrush (*Scirpus juncoides*), needle spikerush (*Eleocharis acicularis*), water nutgrass (*Cyperus serotinus*) and water chestnut (*Eleocharis kuroguwai*);

Waterhyacinths (Pontederiaceous weeds) such as monochoria (*Monochoria vaginalis*);

Waterplantains (Alismataceous weeds) such as arrowhead (*Sagittaria pygmaea*), arrowhead (*Sagittaria trifolia*) and waterplantain (*Alisma canaliculatum*);

Pondweeds (Potamogetonaceous weeds) such as roundleaf pondweed (*Potamogeton distinctus*);

Umbellifers (Umbelloferous weeds) such as watercelery sp. (*Oenanthe javanica*).

Furthermore, some of the present compounds exhibit no significant phytotoxicity on transplanted paddy rice.

The present compounds can also attain the control of weeds which are growing or will grow in the non-cultivated lands such as embankments; riverbanks; roadsides; railways; parks; grounds; parking places; airports; industrial facilities including factories, warehouses and so on; unused farms and unused lands in the city, and in the orchards, grasslands, lawns and forests. The present compounds also have herbicidal activity against various aquatic weeds, such as water hyacinth (*Eichhornia crassipes*), which are growing or will grow in the rivers, waterways, canals, ponds and so on.

The present compounds have the same properties as those of the herbicidal compounds described in the international patent publication WO95/34659. In the case of cultivating crops wherein tolerance is bestowed to the said crops by introducing a herbicide tolerance gene described in the said specification, the present compound can be used at larger amount than those used when ordinary crops without tolerance are cultivated, thus making it possible to control other unfavorable weeds more effectively.

When the present compound is used as the active ingredient of a herbicide, the present compound is usually mixed with solid or liquid carriers, surfactants, and other auxiliary agents to give emulsifiable concentrates, wettable powders, flowables, granules, concentrated emulsions, water-dispersible granules, or other formulations.

These formulations may comprise a compound of present invention as an active ingredient at an amount from 0.001% to 80% by weight, preferably from 0.005% to 70% by weight.

The solid carrier may include, for example, mineral fine powders such as kaolin clay, attapulgite clay, bentonite, acid clay, pyrophyllite, talc, diatomaceous earth, and calcite; organic fine powders such as walnut shell powder; water-soluble organic fine powders such as urea; inorganic salts fine powders such as ammonium sulfate; and fine powders of synthetic hydrated silicon oxide. The liquid carrier may include, for example, aromatic hydrocarbons such as methylnaphthalene, phenylxylylethane, and alkylbenzene (e.g., xylene); alcohols such as 2-propanol, ethylene glycol and 2-ethoxyethanol; esters such as dialkyl phthalate; ketones such as acetone, cyclohexanone, and isophorone; mineral oils such as machine oil; vegetable oils such as soybean oil and cottonseed oil; dimethylsulfoxide; N,N-dimethylformamide; acetonitrile; N-methylpyrrolidone; and water. As the surfactant used for emulsifying, dispersing or spreading; anionic surfactants such as alkylsulfate salts, alkylsulfonate salts, alkylarylsulfonate salts, dialkylsulfosuccinate salts and polyoxyethylenealkyl aryl ether phosphate salts and nonionic surfactants such as polyoxyethylenealkyl ethers, polyoxyethylenealkyl aryl ethers, polyoxyethylene polyoxypropylene block copolymers, sorbitan fatty acid esters and polyoxyethylene sorbitan fatty acid esters are set forth.

Ligninsulfonates, alginates, polyvinyl alcohol, gum arabic, CMC (carboxymethylcellulose), and PAP (isopropyl acid phosphate) and the like are set forth as the possible auxiliary agents, for example.

The present compound is usually formulated and then used for soil treatment before or after the emergence of weeds. The soil treatment may be include a soil surface treatment and a soil incorporation treatment. The foliar treatment may be include application over the plants and directed application in which it is applied only to weeds so as to keep off the crop plants.

Furthermore, by intermixing other herbicides, there are situations wherein an enhanced the herbicidal efficasy is confirmed. Furthermore, the present compound may be used in admixture with insecticides, acaricides, nematocides, fungicides/bactericides, plant growth regulators, fertilizers, and soil improvements.

Examples of the herbicides are atrazine, cyanazine, dimethametryn, metribuzin, prometryn, simazine, simetryn, chlorotoluron, diuron, fluometuron, isoproturon, linuron, methabenzthiazuron, propanil, bentazone, bromoxynil, ioxynil, pyridate, butamifos, dithiopyr, ethalfluralin, pendimethalin, thiazopyr, trifluralin, acetochlor, alachlor, butachlor, diethatyl-ethyl, dimethenamid, fluthiamid, mefenacet, metolachlor, pretilachlor, propachlor, cinmethylin, acifluorfen, acifluorfen-sodium, benzfendizone, bifenox, butafenacil, chlomethoxynil, fomesafen, lactofen, oxadiazon, oxadiargyl, oxyfluorfen, carfentrazone-ethyl, fluazolate, flumiclorac-pentyl, flumioxazine, fluthiacet-methyl, isopropazol, sulfentrazone, thidiazimin, azafenidin, pyraflufen-ethyl, cinidon-ethyl, difenzoquat, diquat, paraquat, 2,4-D, 2,4-DB, clopyralid, dicamba, fluroxypyr, MCPA, MCPB, mecoprop, quinclorac, triclopyr, azimsulfuron, bensulfuron-methyl, chlorimuron-ethyl, chlorsulfuron, cloransulam-methyl, cyclosulfamuron, diclosulam, ethoxysulfuron, flazasulfuron, flucarbazone, flumetsulam, flupyrsulfuron, halosulfuron-methyl, imazosulfuron, iodosulfuron, metosulam, metsulfuron-methyl, nicosulfuron, oxasulfuron, primisulfuron-methyl, procarbazone-sodium, prosulfuron, pyrazosulfuron-ethyl, rimsulfuron, sulfometuron-methyl, sulfosulfuron, triasulfuron, tribenuron-methyl, tritosulfuron, thifensulfuron-methyl, triflusulfuron-methyl, pyribenzoxim, bispyribac-sodium, pyriminobac-methyl, pyrithiobac-sodium, imazameth, imazamethabenz-methyl, imazamox, imazapic, imazapyr, imazaquin, imazethapyr, tepraloxydim, alloxydim-sodium, clethodim, clodinafop-propargyl, cyhalofop-butyl, dichlofop-methyl, fenoxaprop-ethyl, fenoxaprop-p-ethyl, fluazifop-butyl, fluazifop-p-butyl, haloxyfop-methyl, quizalofop-p-ethyl, sethoxydim, tralkoxydim, diflufenican, flurtamone, norflurazon, benzofenap, isoxaflutole, pyrazolate, pyrazoxyfen, sulcotrione, clomazone, mesotrione, isoxachlortole, bialaphos, glufosinate-ammonium, glyphosate, sulfosate, dichlobenil, isoxaben, benthiocarb, butylate, dimepiperate, EPTC, esprocarb, molinate, pyributicarb, triallate, diflufenzopyr, bromobutide, DSMA, MSMA, cafenstrol, daimuron, epoprodan, flupoxam, metobenzuron, pentoxazone, piperophos, triaziflam, beflubutamid, benzobicyclon, clomeprop, fentrazamide, flufenacet, florasulam, indanofen, isoxadifen, mesotrione, naploanilide, oxaziclomefone, pethoxyamid, phenothiol and pyridafol.

The above compounds are disclosed in the catalog of Farm Chemicals Handbook, 1995 (published by Meister Publishing Company); AG CHEM NEW COMPOUND REVIEW, VOL. 13, 1995 (published by AG CHEM INFORMATION SERVICES); AG CHEM NEW COMPOUND REVIEW, VOL. 15, 1997 (published by AG CHEM INFORMATION SERVICES); AG CHEM NEW COMPOUND REVIEW, VOL. 16, 1998 (published by AG CHEM INFORMATION SERVICES); AG CHEM NEW COMPOUND REVIEW, VOL. 17, 1999 (published by AG CHEM INFORMATION SERVICES); and "Josouzai Kenkyu Souran" (published by Hakuyu-sha).

In the case when the present compound is utilized as an active ingredient of an herbicide, the application dosage may vary with the weather conditions, formulation types, application timing, application method, soil conditions, objective crops and objective weeds, but is usually applied at 0.01 g to 20,000 g, preferably 1 g to 12,000 g per hectare. When the present compound is formulated into emulsifiable concentrates, wettable powders, flowables, concentrated emulsions, water-dispersible granules, or the like, the said formulations are applied by diluting the present compound usually in 10 L to 1000 L of water (if necessary, the water may include an adjuvant such as a spreading agent) so the prescribed amount of the active ingredient can be applied to each hectare. Granules and some types of flowables are usually applied without diluting. The adjuvant which can be used herein, if necessary, may include, in addition to the surfactants as described above, polyoxyethylene resin acids (esters), ligninsulfonates, abietates, dinaphthylmethanedisulfonates, crop oil concentrates, and vegetable oils such as soybean oil, corn oil, cottonseed oil, and sunflower oil.

The present compounds can also be used as the active ingredients of harvesting aids such as defoliants and desiccants for cotton, and desiccants for potato (*Solanum tuberosum*). In these cases, the present compounds are usually formulated in the same manner as the case where they are used as the active ingredients of herbicides, and may be used alone or in admixture with other harvesting aids for foliar treatment before harvesting the crops.

EXAMPLES

Hereinafter, the present invention is explained more specifically by means of the examples, but the said examples do not limit the present invention in any way.

The production examples of the present compounds are given below, wherein the compound numbers of the present compounds are the same numbers as given in the tables 1–10.

Production Example 1

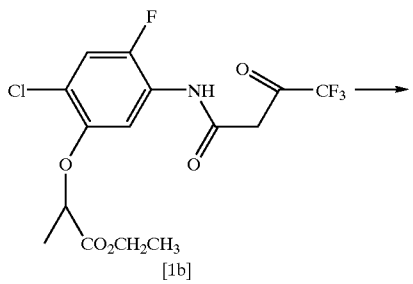

[1b]

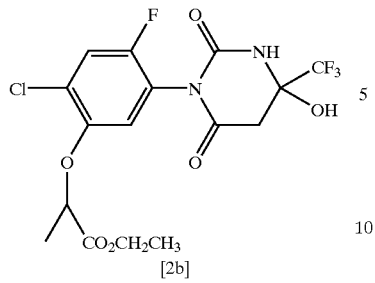

[2b]

To a solution obtained by dissolving 3.56 g of Compound [1b] in 14.5 mL of acetic acid, 1.04 g of sodium cyanate was added and stirred for 2.5 hours at room temperature. Then, water was added to the reaction solution, and the reaction solution was extracted with ethyl acetate. The organic layer was washed with aqueous sodium hydroxide and saturated brine successively, dried over anhydrous magnesium sulfate and concentrated to give a residue, which was subjected to column chromatography (hexane:ethyl acetete=4:1–2:1) to give 3.72 g of Compound [2b] (the present compound 5-25).
Compound [2b] (the present compound 5-25)
$^1$H-NMR (300 MHz, CDCl$_3$, TMS δ(ppm)) 1.18–1.28 (3H,m), 1.62–1.67 (1H,m), 2.97–3.21 (2H,m), 4.08–4.24 (2H,m), 4.65–4.72 (1H,m), 6.74–6.85 (1H,m), 6.89–7.08 (1H,br), 7.26 (1H,d,J=7.42 Hz)

Production Example 2

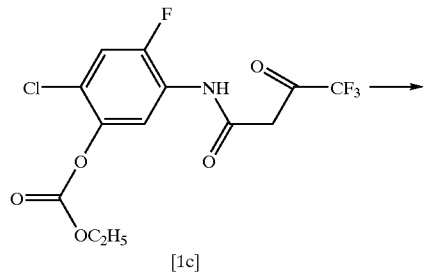

[1c]

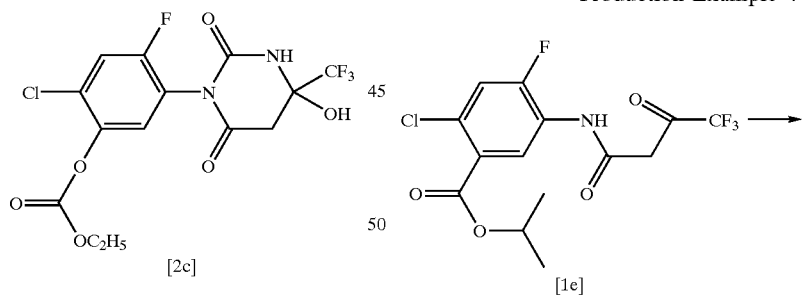

[2c]

To a solution obtained by dissolving 2.72 g of Compound [1c] in 10 mL of acetic acid, 0.79 g of potassium cyanate was added and stirred for 2 hours at room temperature. Then, to the concentrated reaction solution, water and hexane were added and allowed to stand. The precipitated crystals were collected by filtration, washed with water and hexane succesesively and dried to give 2.73 g of Compound [2c] (the present compound 5-68).
Compound [2c] (the present compound 5-68)
m.p. 100.2° C.
$^1$H-NMR (300 MHz, CDCl$_3$, TMS δppm)) 1.40 (3H,t,J= 7.11 Hz), 3.06–3.24 (2H,m), 4.30–4.38 (2H,m), 7.16–7.22 (1H,m), 7.35 (1H,d,J=8.69 Hz)

Production Example 3

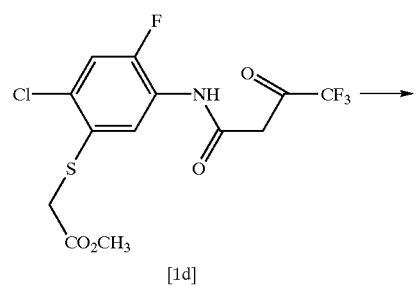

[1d]

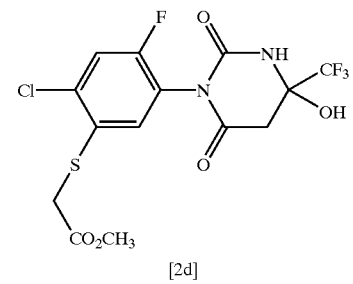

[2d]

To a solution obtained by dissolving 2.50 g of Compound [1d] in 10 mL of acetic acid, 0.70 g of potassium cyanate was added and stirred for 2 hours at room temperature. Then, water was added to the concentrated reaction solution, and the reaction solution was extracted with ethyl acetate. The organic layer was washed with aqueous saturated sodium bicarbonate and saturated brine successively, dried over anhydrous magnesium sulfate and concentrated to give a residue, which was subjected to column chromatography (hexane: ethyl acetete=3:1–1:1) to give 2.68 g of Compound [2d] (the present compound 5-71).
Compound [2d] (the present compound 5-71)
$^1$H-NMR (300 MHz, CDCl$_3$, TMS δppm)) 3.06–3.24 (2H,m), 3.63–3.69 (5H,m), 7.05–7.20 (1H,br), 7.29 (1H,d, J=8.97 Hz), 7.36–7.44 (1H,m)

Production Example 4

[1e]

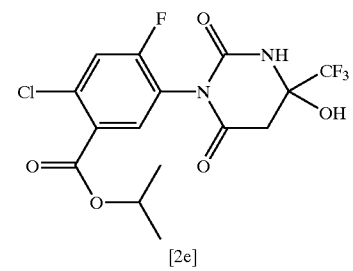

[2e]

To a solution obtained by dissolving 2.65 g of Compound [1e] in 10 mL of acetic acid, 0.78 g of potassium cyanate was added and stirred for 10.5 hours at room temperature. Then, water was added to the concentrated reaction solution, and the reaction solution was extracted with ethyl acetate. The organic layer was washed with aqueous saturated sodium bicarbonate and saturated brine successively, dried over anhydrous magnesium sulfate and concentrated to give crystals, which were washed with hexane to give 2.61 g of Compound [2e] (the present compound 6-19).
Compound [2e] (the present compound 6-19).
m.p. 151.1° C.
¹H-NMR (300 MHz, CDCl₃, TMS δppm)) 1.35–1.40 (6H,m), 3.13–3.27 (2H,m), 5.18–5.32 (1H,m), 7.34 (1H,d, J=10.9 Hz), 7.78 (1H,d,J=9.30 Hz)

Production Example 5

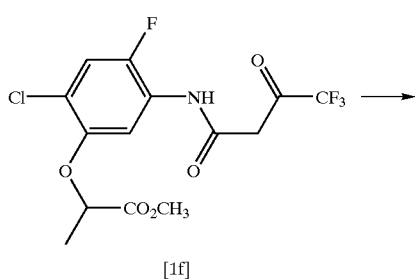

[1f]

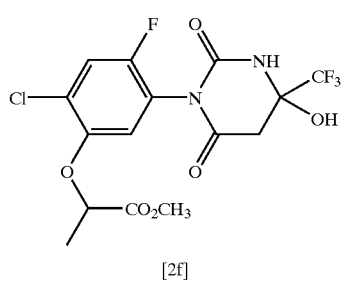

[2f]

To a solution obtained by dissolving 2.68 g of Compound [1f] in 10 mL of acetic acid, 0.75 g of potassium cyanate was added and stirred for 3.5 hours at room temperature. Then, water was added to the concentrated reaction solution, and the reaction solution was extracted with ethyl acetate. The organic layer was washed with aqueous saturated sodium bicarbonate and saturated brine successively, dried over anhydrous magnesium sulfate and concentrated to give a residue, which was subjected to column chromatography (hexane: ethyl acetete=3:1–1:1) to give 2.84 g of Compound [2f] (the present compound 5-24).
Compound [2f] (the present compound 5-24)
¹H-NMR (300 MHz, CDCl₃, TMS δppm)) 1.64–1.68 (3H,m), 3.00–3.16 (2H,m), 3.72–3.75 (3H,m), 4.67–4.74 (1H,m), 6.73–6.84 (1H,m), 6.84–7.10 (1H,br), 7.28 (1H,d, J=9.17 Hz)

Production Example 6

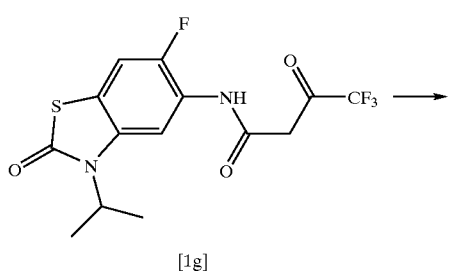

[1g]

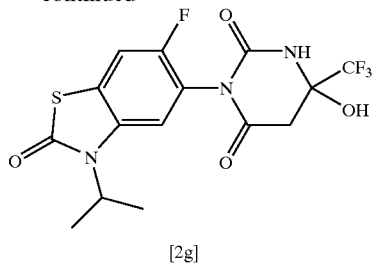

[2g]

To a solution obtained by dissolving 2.87 g of Compound [1g] in 12 mL of acetic acid, 0.89 g of potassium cyanate was added and stirred for 4.5 hours at room temperature. Then, water was added to the concentrated reaction solution, and the reaction solution was extracted with ethyl acetate. The organic layer was washed with aqueous saturated sodium bicarbonate and saturated brine successively, dried over anhydrous magnesium sulfate and concentrated to give crystals, which were washed with hexane to give 3.14 g of Compound [2g] (the present compound 3-16).

Compound [2g] (the present compound 3-16)
m.p. 152.7° C.
¹H-NMR (300 MHz, CDCl₃, TMS δppm)) 1.56 (6H,d,J= 6.92 Hz), 3.14–3.33 (2H,m), 4.60–4.72 (1H,m), 6.78–6.86 (1H,m), 6.99–7.03 (1H,m), 7.31 (1H,d,J=8.48 Hz)

Production Example 7

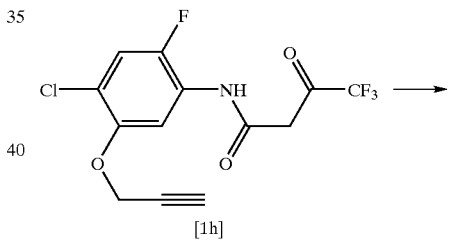

[1h]

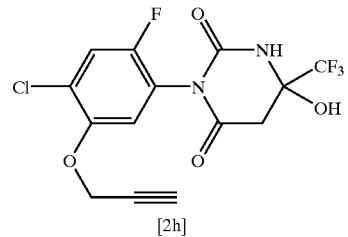

[2h]

To a solution obtained by dissolving 2.51 g of Compound [1h] in 10 mL of acetic acid, 0.80 g of potassium cyanate was added and stirred for 3.5 hours at room temperature. Then, the reaction solution was concentrated to give crystals, which were washed with hexane to give 2.25 g of Compound [2h] (the present compound 5-14).

Compound [2h] (the present compound 5-14)
m.p. 151.9° C.
¹H-NMR (300 MHz, CDCl₃, TMS δppm)) 2.57 (1H,s), 3.09–3.29 (2H,m), 4.72–4.75 (2H,m), 6.65 (1H,br), 6.92–6.96 (1H,m), 7.29 (1H,d,J=8.68 Hz)

Production Example 8

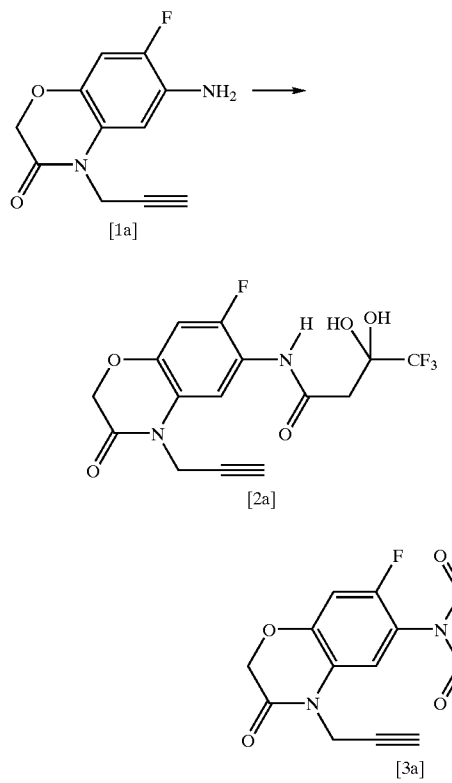

To 150 mL of toluene, 33.0 g of Compound [1a] and 30.3 g of ethyl 4,4,4-trifluoroacetoacetate were added and stirred with heating under reflux for 4 hours. Then, the reaction solution was concentrated under a reduced pressure. The obtained residue was dissolved in ethyl acetate. The ethyl acetate solution was washed with conc. HCl and water successively, dried over anhydrous magnesium sulfate and concentrated under a reduced pressure to give 35.7 g of Compound [2a].

Compound [2a]

m.p. 110.4° C.

To 30 mL of acetic acid, 7.16 g of Compound [2a] and 1.8 g of potassium cyanate were added and stirred at room temperature overnight (for about 12 hours). Then, the reaction solution was poured into water and extracted with ethyl acetate. The organic layer was washed with aqueous saturated sodium bicarbonate, dried over anhydrous magnesium sulfate and concentrated under a reduced pressure to give 7.17 g of Compound [3a] present compound 3-3).

Compound [3a] (the present compound 3-3)

$^1$H-NMR (300 MHz, CDCl$_3$, TMS δppm)) 2.26–2.30 (1H,m), 2.32–2.53 (1H,br), 3.08–3.26 (2H,m), 4.59–4.69 (4H,m), 6.78–6.88 (1H,br), 6.85–6.90 (1H,m), 6.99–7.02 (1H,m)

Some of the present compounds which are obtainable according to Production examples 1–8 are listed below, but the present invention should not be limited to them.

TABLE 1

Compounds given by formula [I-1]

[I-1]

| Compound Nos. | Z | $R^3$ | $R^4$ | $R^{12}$ |
|---|---|---|---|---|
| 1-1 | O | F | Cl | H |
| 1-2 | O | F | Cl | $CO_2CH_3$ |
| 1-3 | O | F | Cl | $CO_2C_2H_5$ |
| 1-4 | O | F | Cl | $CO_2CH(CH_3)_2$ |
| 1-5 | O | F | Cl | $CO_2(CH_2)_3CH_3$ |
| 1-6 | O | F | Cl | $CO_2(CH_2)_4CH_3$ |
| 1-7 | O | Cl | Cl | H |
| 1-8 | O | Cl | Cl | $CO_2CH_3$ |
| 1-9 | O | Cl | Cl | $CO_2C_2H_5$ |
| 1-10 | O | Cl | Cl | $CO_2CH(CH_3)_2$ |
| 1-11 | O | Cl | Cl | $CO_2(CH_2)_3CH_3$ |
| 1-12 | O | Cl | Cl | $CO_2(CH_2)_3CH_3$ |
| 1-13 | O | F | Cl | $CH_2OCH_3$ |
| 1-14 | O | H | Cl | H |
| 1-15 | O | H | Cl | $CO_2CH_3$ |
| 1-16 | O | H | Cl | $CO_2C_2H_5$ |
| 1-17 | O | H | Cl | $CO_2(CH_3)_2$ |
| 1-18 | O | H | Cl | $CO_2(CH_2)_3CH_3$ |
| 1-19 | O | H | Cl | $CO_2(CH_2)_3CH_3$ |
| 1-20 | S | F | Cl | H |
| 1-21 | S | F | Cl | $CO_2CH_3$ |
| 1-22 | S | F | Cl | $CO_2C_2H_5$ |
| 1-23 | S | F | Cl | $CO_2CH(CH_3)_2$ |

TABLE 2

Compounds given by formula [I-2]

[I-2]

| Compound Nos. | Z | $R^3$ | $R^4$ | $R^{13}$ | $R^{14}$ |
|---|---|---|---|---|---|
| 2-1 | O | F | Cl | H | H |
| 2-2 | O | F | Cl | H | $CO_2CH_3$ |
| 2-3 | O | F | Cl | H | $CO_2C_2H_5$ |
| 2-4 | O | F | Cl | H | $CO_2CH(CH_3)_2$ |
| 2-5 | O | F | Cl | H | $CO_2(CH_2)_3CH_3$ |
| 2-6 | O | F | Cl | H | $CO_2(CH_2)_4CH_3$ |
| 2-7 | O | F | Cl | $CH_3$ | H |
| 2-8 | O | F | Cl | $CH_3$ | $CO_2CH_3$ |
| 2-9 | O | F | Cl | $CH_3$ | $CO_2C_2H_5$ |
| 2-10 | O | F | Cl | $CH_3$ | $CO_2CH(CH_3)_2$ |
| 2-11 | O | F | Cl | $CH_3$ | $CO_2(CH_2)_3CH_3$ |
| 2-12 | O | F | Cl | $CH_3$ | $CO_2(CH_2)_4CH_3$ |
| 2-13 | O | F | Cl | $CH_3$ | $CH_2OC(=O)CH_3$ |
| 2-14 | O | H | Cl | H | H |
| 2-15 | O | H | Cl | H | $CO_2CH_3$ |
| 2-16 | O | H | Cl | H | $CO_2C_2H_5$ |

TABLE 2-continued

Compounds given by formula [I-2]

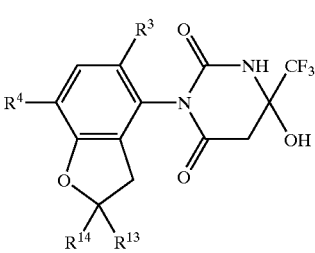

[I-2]

| Compound Nos. | Z | $R^3$ | $R^4$ | $R^{13}$ | $R^{14}$ |
|---|---|---|---|---|---|
| 2-17 | O | H | Cl | H | $CO_2CH(CH_3)_2$ |
| 2-18 | O | H | Cl | H | $CO_2(CH_2)_3CH_3$ |
| 2-19 | O | H | Cl | H | $CO_2(CH_2)_4CH_3$ |
| 2-20 | O | H | Cl | $CH_3$ | H |
| 2-21 | O | H | Cl | $CH_3$ | $CO_2CH_3$ |
| 2-22 | O | H | Cl | $CH_3$ | $CO_2C_2H_5$ |
| 2-23 | O | H | Cl | $CH_3$ | $CO_2CH(CH_3)_2$ |

TABLE 3

Compounds given by formula [I-3]

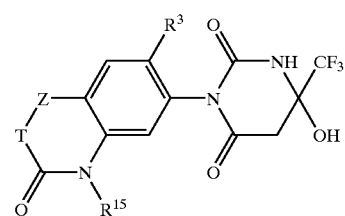

[I-3]

| Compound Nos. | Z | $R^3$ | T | $R^{15}$ |
|---|---|---|---|---|
| 3-1 | O | F | $CH_2$ | $CH_3$ |
| 3-2 | O | F | $CH_2$ | $CH(CH_3)_2$ |
| 3-3 | O | F | $CH_2$ | $CH_2C{\equiv}CH$ |
| 3-4 | O | F | $CH_2$ | $CH(CH_3)C{\equiv}CH$ |
| 3-5 | O | F | $CH_2$ | $CH_2CH{=}CH_2$ |
| 3-6 | O | F | $CH_2$ | $CH_2CH_2F$ |
| 3-7 | O | F | $CH_2$ | $CH_2OCH_3$ |
| 3-8 | O | H | $CH_2$ | $CH_3$ |
| 3-9 | O | H | $CH_2$ | $CH(CH_3)_2$ |
| 3-10 | O | H | $CH_2$ | $CH_2C{\equiv}CH$ |
| 3-11 | O | H | $CH_2$ | $CH(CH_3)C{\equiv}CH$ |
| 3-12 | O | H | $CH_2$ | $CH_2CH{=}CH_2$ |
| 3-13 | O | H | $CH_2$ | $CH_2CH_2F$ |
| 3-14 | O | H | $CH_2$ | $CH_2OCH_3$ |
| 3-15 | S | F | bond | $CH_3$ |
| 3-16 | S | F | bond | $CH(CH_3)_2$ |
| 3-17 | S | F | bond | $CH_2C{\equiv}CH$ |
| 3-18 | S | F | bond | $CH(CH_3)C{\equiv}CH$ |
| 3-19 | S | F | bond | $CH_2CH{=}CH_2$ |
| 3-20 | S | F | bond | $CH_2CH_2F$ |
| 3-21 | S | F | bond | $CH_2OCH_3$ |
| 3-22 | S | F | bond | $CH(CH_3)CO_2CH_3$ |
| 3-23 | S | F | bond | $CH(CH_3)CO_2C_2H_5$ |

TABLE 4

Compounds given by formula [I-4]

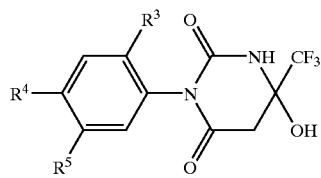

[I-4]

| Compound Nos. | $R^3$ | $R^4$ | $R^5$ |
|---|---|---|---|
| 4-1 | F | $C{\equiv}CH$ | H |
| 4-2 | F | F | H |
| 4-3 | F | Cl | H |
| 4-4 | F | Br | H |
| 4-5 | F | CN | H |
| 4-6 | F | $NO_2$ | H |
| 4-7 | Cl | Cl | H |
| 4-8 | F | F | $NO_2$ |
| 4-9 | Cl | Cl | $NO_2$ |
| 4-10 | F | CN | $NO_2$ |
| 4-11 | F | CN | F |
| 4-12 | F | Br | $NO_2$ |
| 4-13 | F | F | F |
| 4-14 | Cl | Cl | Cl |
| 4-15 | H | F | $NO_2$ |
| 4-16 | H | Cl | $NO_2$ |
| 4-17 | H | Br | $NO_2$ |
| 4-18 | H | CN | $NO_2$ |
| 4-19 | H | $NO_2$ | F |

TABLE 5

Compounds given by formula [I-5]

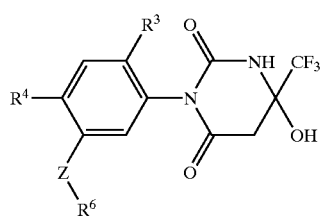

[I-5]

| Compound Nos. | Z | $R^3$ | $R^4$ | $R^6$ |
|---|---|---|---|---|
| 5-1 | O | H | Cl | $CH(CH_3)_2$ |
| 5-2 | O | H | Br | $CH(CH_3)_2$ |
| 5-3 | O | H | CN | $CH(CH_3)_2$ |
| 5-4 | O | H | F | $CH(CH_3)_2$ |
| 5-5 | O | H | Cl | $CH(CH_3)CO_2CH_3$ |
| 5-6 | O | H | Cl | $CH(CH_3)CO_2C_2H_5$ |
| 5-7 | O | H | Cl | $CH_2C{\equiv}CH$ |
| 5-8 | O | H | Cl | $CH(CH_3)C{\equiv}CH$ |
| 5-9 | O | H | Cl | $CH_2CO_2CH_3$ |
| 5-10 | O | H | Cl | $CH_2CO_2C_2H_5$ |
| 5-11 | O | F | Cl | $CH_3$ |
| 5-12 | O | F | Cl | $CH(CH_3)_2$ |
| 5-13 | O | F | Cl | $CH_2CH{=}CH_2$ |
| 5-14 | O | F | Cl | $CH_2C{\equiv}CH$ |
| 5-15 | O | F | Cl | $CH(CH_3)C{\equiv}CH$ |
| 5-16 | O | F | Cl | $CH_2CO_2CH_3$ |
| 5-17 | O | F | Cl | $CH_2CO_2C_2H_5$ |
| 5-18 | O | F | Cl | $CH_2CO_2(CH_2)_2CH_3$ |
| 5-19 | O | F | Cl | $CH_2CO_2CH(CH_3)_2$ |
| 5-20 | O | F | Cl | $CH_2CO_2(CH_2)_3CH_3$ |
| 5-21 | O | F | Cl | $CH_2CO_2CH(CH_3)C_2H_5$ |
| 5-22 | O | F | Cl | $CH_2CO_2(CH_2)_4CH_3$ |
| 5-23 | O | F | Cl | $CH_2CO_2(CH_2)_5CH_3$ |
| 5-24 | O | F | Cl | $CH(CH_3)CO_2CH_3$ |

TABLE 5-continued

Compounds given by formula [I-5]

| Compound Nos. | Z | $R^3$ | $R^4$ | $R^6$ |
|---|---|---|---|---|
| 5-25 | O | F | Cl | $CH(CH_3)CO_2C_2H_5$ |
| 5-26 | O | F | Cl | $CH(CH_3)CO_2(CH_2)_2CH_3$ |
| 5-27 | O | F | Cl | $CH(CH_3)CO_2CH(CH_3)_2$ |
| 5-28 | O | F | Cl | $CH(CH_3)CO_2(CH_2)_3CH_3$ |
| 5-29 | O | F | Cl | $CH(CH_3)CO_2CH(CH_3)C_2H_5$ |
| 5-30 | O | F | Cl | $CH(CH_3)CO_2(CH_2)_4CH_3$ |
| 5-31 | O | F | Cl | $CH(CH_3)CO_2(CH_2)_5CH_3$ |
| 5-32 | O | F | Cl | $CH(CH_3)CO_2CH_2OCH_3$ |
| 5-33 | O | F | Cl | $CH(CH_3)CO_2CH_2OC_2H_5$ |
| 5-34 | O | F | Cl | $CH(CH_3)CO_2CH_2CH_2OCH_3$ |
| 5-35 | O | F | Cl | $CH(CH_3)CO_2CH_2CH_2OC_2H_5$ |
| 5-36 | O | F | Cl | $CH_2OCH_3$ |
| 5-37 | O | F | Cl | $CH_2OC_2H_5$ |
| 5-38 | O | F | Cl | $CH_2CH_2F$ |
| 5-39 | O | F | Cl | $CH(CH_3)C{\equiv}CH$ (R-isomer) |
| 5-40 | O | F | Cl | $CH(CH_3)C{\equiv}CH$ (S-isomer) |
| 5-41 | O | F | Cl | $CH(CH_3)CO_2CH_3$ (R-isomer) |
| 5-42 | O | F | Cl | $CH(CH_3)CO_2CH_3$ (S-isomer) |
| 5-43 | O | F | Cl | $CH(CH_3)CO_2C_2H_5$ (R-isomer) |
| 5-44 | O | F | Cl | $CH(CH_3)CO_2C_2H_5$ (S-isomer) |
| 5-45 | O | F | Cl | $CH(CH_3)CO_2(CH_2)_2CH_3$ (R-isomer) |
| 5-46 | O | F | Cl | $CH(CH_3)CO_2(CH_2)_2CH_3$ (S-isomer) |
| 5-47 | O | F | Cl | $CH(CH_3)CO_2CH(CH_3)C_2H_5$ (R-isomer) |
| 5-48 | O | F | Cl | $CH(CH_3)CO_2CH(CH_3)C_2H_5$ (S-isomer) |
| 5-49 | O | F | Cl | Ph-2-$(OCH_2CO_2CH_3)$ |
| 5-50 | O | F | Cl | Ph-2-$(OCH_2CO_2C_2H_5)$ |
| 5-51 | O | F | Cl | Ph-2-$(OCH_2CO_2(CH_2)_2CH_3)$ |
| 5-52 | O | F | Cl | Ph-3-$(OCH_2CO_2CH_3)$ |
| 5-53 | O | F | Cl | Ph-3-$(OCH_2CO_2C_2H_5)$ |
| 5-54 | O | F | Cl | Ph-3-$(OCH_2CO_2(CH_2)_2CH_3)$ |
| 5-55 | O | F | Cl | Ph-4-$(OCH_2CO_2CH_3)$ |
| 5-56 | O | F | Cl | Ph-4-$(OCH_2CO_2C_2H_5)$ |
| 5-57 | O | F | Cl | Ph-4-$(OCH_2CO_2(CH_2)_2CH_3)$ |
| 5-58 | O | F | Cl | Ph-2-$(OCH(CH_3)CO_2CH_3)$ |
| 5-59 | O | F | Cl | Ph-2-$(OCH(CH_3)CO_2C_2H_5)$ |
| 5-60 | O | F | Cl | Ph-2-$(OCH(CH_3)CO_2(CH_2)_2CH_3)$ |
| 5-61 | O | F | Cl | Ph-3-$(OCH(CH_3)CO_2CH_3)$ |
| 5-62 | O | F | Cl | Ph-3-$(OCH(CH_3)CO_2C_2H_5)$ |
| 5-63 | O | F | Cl | Ph-3-$(OCH(CH_3)CO_2(CH_2)_2CH_3)$ |
| 5-64 | O | F | Cl | Ph-4-$(OCH(CH_3)CO_2CH_3)$ |
| 5-65 | O | F | Cl | Ph-4-$(OCH(CH_3)CO_2C_2H_5)$ |
| 5-66 | O | F | Cl | Ph-4-$(OCH(CH_3)CO_2(CH_2)_2CH_3)$ |
| 5-67 | O | F | Cl | $CO_2CH_3$ |
| 5-68 | O | F | Cl | $CO_2C_2H_5$ |
| 5-69 | S | F | Cl | $CH_3$ |
| 5-70 | S | F | Cl | $C_2H_5$ |
| 5-71 | S | F | Cl | $CH_2CO_2CH_3$ |
| 5-72 | S | F | Cl | $CH(CH_3)CO_2CH_3$ |
| 5-73 | S | F | Cl | $CH_2C{\equiv}CH$ |

TABLE 6

Compounds given by formula [I-6]

| Compound Nos. | $R^3$ | $R^4$ | $R^7$ |
|---|---|---|---|
| 6-1 | H | Cl | $OCH_2CH{=}CH_2$ |
| 6-2 | H | Cl | $OCH_3$ |
| 6-3 | H | Cl | $OC_2H_5$ |
| 6-4 | H | Cl | $O(CH_2)_2CH_3$ |
| 6-5 | H | Cl | $OCH(CH_3)_2$ |
| 6-6 | H | Cl | $OCH_2CO_2CH_3$ |
| 6-7 | H | Cl | $OCH_2CO_2C_2H_5$ |
| 6-8 | H | Cl | $OCH_2CO_2CH_2CH{=}CH_2$ |
| 6-9 | H | Cl | $OCH_2CO_2CH_2C{\equiv}CH$ |
| 6-10 | H | Cl | $OCH(CH_3)CO_2CH_3$ |
| 6-11 | H | Cl | $OCH(CH_3)CO_2C_2H_5$ |
| 6-12 | H | Cl | $OCH(CH_3)CO_2CH_2CH{=}CH_2$ |
| 6-13 | H | Cl | $OCH(CH_3)CO_2CH_2C{\equiv}CH$ |
| 6-14 | H | Cl | $OC(CH_3)_2CO_2CH_3$ |
| 6-15 | H | Cl | $OC(CH_3)_2CO_2C_2H_5$ |
| 6-16 | H | Cl | $OC(CH_3)_2CO_2CH_2CH{=}CH_2$ |
| 6-17 | H | Cl | $OC(CH_3)_2CO_2CH_2C{\equiv}CH$ |
| 6-18 | F | Cl | $OCH_2CH{=}CH_2$ |
| 6-19 | F | Cl | $OCH(CH_3)_2$ |
| 6-20 | F | Cl | $OCH_2CO_2CH_2CH{=}CH_2$ |
| 6-21 | F | Cl | $OCH_2CO_2CH_2C{\equiv}CH$ |
| 6-22 | F | Cl | $OC(CH_3)_2CO_2CH_2CH{=}CH_2$ |
| 6-23 | F | Cl | $OC(CH_3)_2CO_2CH_2C{\equiv}CH$ |

TABLE 7

Compounds given by formula [I-7]

| Compound Nos. | $R^3$ | $R^4$ | $R^9$ | $R^8$ |
|---|---|---|---|---|
| 7-1 | H | Cl | H | $OCH_3$ |
| 7-2 | H | Cl | H | $OC_2H_5$ |
| 7-3 | H | Cl | H | $O(CH_2)_2CH_3$ |
| 7-4 | H | Cl | H | $OCH(CH_3)_2$ |
| 7-5 | H | Cl | H | $O(CH_2)_3CH_3$ |
| 7-6 | H | Cl | H | $O(CH_2)_4CH_3$ |
| 7-7 | H | Cl | Cl | $OCH_3$ |
| 7-8 | H | Cl | Cl | $OC_2H_5$ |
| 7-9 | H | Cl | Cl | $O(CH_2)_2CH_3$ |
| 7-10 | H | Cl | Cl | $OCH(CH_3)_2$ |
| 7-11 | H | Cl | Cl | $O(CH_2)_3CH_3$ |
| 7-12 | H | Cl | Cl | $O(CH_2)_4CH_3$ |
| 7-13 | F | Cl | H | $OCH_3$ |
| 7-14 | F | Cl | H | $OC_2H_5$ |
| 7-15 | F | Cl | H | $O(CH_2)_2CH_3$ |
| 7-16 | F | Cl | H | $OCH(CH_3)_2$ |
| 7-17 | F | Cl | H | $O(CH_2)_3CH_3$ |

TABLE 7-continued

Compounds given by formula [I-7]

[I-7]

| Compound Nos. | $R^3$ | $R^4$ | $R^9$ | $R^8$ |
|---|---|---|---|---|
| 7-18 | F | Cl | Cl | $OCH_3$ |
| 7-19 | F | Cl | Cl | $OC_2H_5$ |
| 7-20 | F | Cl | Cl | $O(CH_2)_2CH_3$ |
| 7-21 | F | Cl | Cl | $OCH(CH_3)_2$ |
| 7-22 | F | Cl | Cl | $O(CH_2)_3CH_3$ |
| 7-23 | F | Cl | Cl | $O(CH_2)_4CH_3$ |

TABLE 8

Compounds given by formula [I-8]

[I-8]

| Compound Nos. | $R^3$ | $R^4$ | $R^{11}$ | $R^{10}$ |
|---|---|---|---|---|
| 8-1 | H | Cl | H | $OCH_3$ |
| 8-2 | H | Cl | H | $OC_2H_5$ |
| 8-3 | H | Cl | H | $OC_3H_7$ |
| 8-4 | H | Cl | H | $OCH(CH_3)_2$ |
| 8-5 | H | Cl | H | $O(CH_2)_3CH_3$ |
| 8-6 | H | Cl | H | $O(CH_2)_4CH_3$ |
| 8-7 | H | Cl | Cl | $OCH_3$ |
| 8-8 | H | Cl | Cl | $OC_2H_5$ |
| 8-9 | H | Cl | Cl | $O(CH_2)_2CH_3$ |
| 8-10 | H | Cl | Cl | $OCH(CH_3)_2$ |
| 8-11 | H | Cl | Cl | $O(CH_2)_3CH_3$ |
| 8-12 | H | Cl | Cl | $O(CH_2)_4CH_3$ |
| 8-13 | F | Cl | H | $OCH_3$ |
| 8-14 | F | Cl | H | $OC_2H_5$ |
| 8-15 | F | Cl | H | $O(CH_2)_2CH_3$ |
| 8-16 | F | Cl | H | $OCH(CH_3)_2$ |
| 8-17 | F | Cl | H | $O(CH_2)_3CH_3$ |
| 8-18 | F | Cl | Cl | $OCH_3$ |
| 8-19 | F | Cl | Cl | $OC_2H_5$ |
| 8-20 | F | Cl | Cl | $O(CH_2)_2CH_3$ |
| 8-21 | F | Cl | Cl | $OCH(CH_3)_2$ |
| 8-22 | F | Cl | Cl | $O(CH_2)_3CH_3$ |
| 8-23 | F | Cl | Cl | $O(CH_2)_4CH_3$ |

The following are Formulation Examples in which the present compounds are indicated by their compound numbers in Tables 1 to 10 and parts are by weight.

Formulation Example 1

Fifty parts of each of the present compounds 3-3, 3-16 and 6-5, 3 parts of calcium ligninsulfonate, 2 parts of sodium laurylsulfate, and 45 parts of synthetic hydrated silicon oxide are well pulverized and mixed to give a wettable powder for each compound.

Formulation Example 2

Ten parts of each of the present compounds 3-3, 3-16 and 6-5, 14 parts of polyoxyethylene styryl phenyl ether, 6 parts of calcium dodecylbenzene-sulfonate, 35 parts of xylene, and 35 parts of cyclohexanone are well mixed to an emulsifiable concentrate for each compound.

Formulation Example 3

Two parts of each of the present compounds 3-3, 3-16 and 6-5, 2 parts of synthetic hydrated silicon oxide, 2 parts of calcium ligninsulfonate, 30 parts of bentonite, and 64 parts of kaolin clay are well pulverized and mixed, and the mixture is well kneaded with water, followed by granulation and drying, to give a granule for each compound.

Formulation Example 4

Twenty-five parts of each of the present compounds 3-3, 3-16 and 6-5, 50 parts of 10% aqueous polyvinyl alcohol solution, and 25 parts of water are mixed and pulverized until the mean particle size reaches 5 μm or smaller to give a flowable for each compound.

Formulation Example 5

Five parts of each of the present compounds 3-3, 3-16 and 6-5 is added to 40 parts of 10% aqueous polyvinyl alcohol solution, and the mixture is emulsified by dispersion with a homogenizer until the mean particle size reaches 10 μm or smaller, followed by addition of 55 parts of water, to give a concentrated emulsion for each compound.

The following are Test Examples for demonstrating that the present compounds are useful as active ingredients of herbicides. The herbicidal activity and phytotoxicity are evaluated at 11 levels with indices of 0 (no effect) to 10 (died completely or their germination or growth was completely inhibited), and the herbicidal activity is judged to be excellent when ranked at 7 or more. The present compounds are designated by their compound numbers shown in Tables 1 to 10.

Test Example 1

Foliar Treatment on Upland Fields

Cylindrical plastic pots each having a diameter of 10 cm and a depth of 10 cm were filled with soil, and then seeded with ivyleaf morningglory (*Ipomoea hederacea*). The test plant was grown in a greenhouse for 14 days. Each of the present compounds 3-3, 3-16 and 6-5 was formulated into an emulsifiable concentrate according to Formulation Example 2, and then diluted in its prescribed amount with water containing a spreading agent. The dilution was uniformly sprayed over the foliage of the test plants with a sprayer at a rate of 1000 liters per hectare. After the application, the test plant was grown in the greenhouse for 12 days, and the herbicidal activity was examined. As a result, all the present compounds 3-3, 3-16 and 6-5 showed excellent activity against ivyleaf morningglory at a dosage of 20 g/are.

Test Example 2

Soil Surface Treatment on Upland Fields

Cylindrical plastic pots each having a diameter of 10 cm and a depth of 10 cm were filled with soil, and then seeded with ivyleaf morningglory (*Ipomoea hederacea*). Each of the present compounds 3-3 and 3-16 was formulated into an emulsifiable concentrate according to Formulation Example 2, and then diluted in its prescribed amount with water. The dilution was uniformly sprayed over the soil surface in the pots with a sprayer at a rate of 1000 liters per hectare. After the application, the test plant were grown in a greenhouse for 12 days, and the herbicidal activity was examined. As a result, both of the present compounds 3-3 and 3-16 showed excellent inhibition of germination against ivyleaf morningglory at a dosage of 80 g/are.

What is claimed is:

1. A 5,6-dihydrouracil compound represented by the formula [I]:

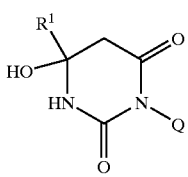

[I]

wherein $R^1$ represents C1–C2 haloalkyl group and Q represents any group of Q1 to Q8 represented by the formulae below:

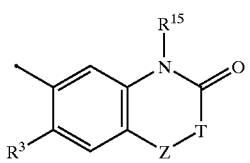 Q1

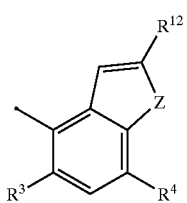 Q2

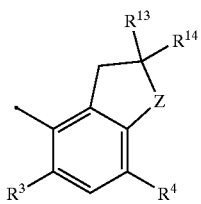 Q3

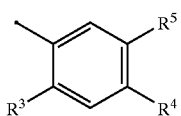 Q4

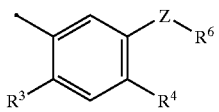 Q5

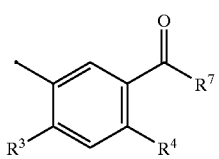 Q6

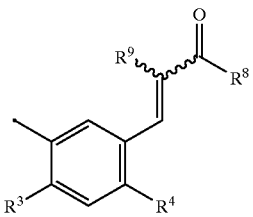 Q7

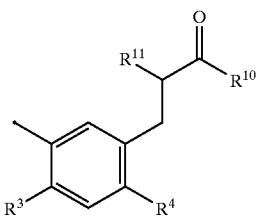 Q8 wherein Z represents oxygen atom, sulfur atom or NH group; T represents direct bond or methylene group;
$R^3$ represents hydrogen atom or halogen atom; $R^4$ represents hydrogen atom, halogen atom, cyano group, nitro group, ethynyl group or a group given by the formula:

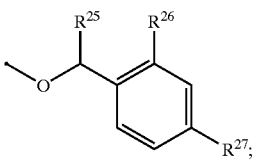

$R^5$ represents hydrogen atom, C1–C6 alkyl group, halogen atom, cyano group, nitro group or hydroxy group; $R^6$ represents C1–C6 alkyl group, C1–C6 haloalkyl group, C3–C8 cycloalkyl group, (C3–C8 cycloalkyl) C1–C3 alkyl group, C3–C6 alkenyl group, C3–C6 alkynyl group, cyano C1–C3 alkyl group, (C1–C3 alkoxy) C1–C3 alkyl group, (C1–C3 alkylthio) C1–C3 alkyl group, (C1–C6 alkyl) carbonyl group, (C1–C6 haloalkyl)carbonyl group, (C3–C8 cycloalkyl)carbonyl group, carboxy C1–C3 alkyl group, (C1–C6 alkoxy)carbonyl C1–C3 alkyl group, (C1–C6 haloalkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, C1–C3 alkoxy (C1–C3 alkoxy)carbonyl C1–C3 alkyl group, carboxy (C1–C3 alkoxy)carbonyl C1–C3 alkyl group, (C1–C6 alkoxy)carbonyl (C1–C3 alkoxy)carbonyl C1–C3 alkyl group, (C1–C6 haloalkoxy)carbonyl (C1–C3 alkoxy) carbonyl C1–C3 alkyl group, (C3–C6 alkenyloxy)carbonyl (C1–C3 alkoxy)carbonyl C1–C3 alkyl group, (C3–C6 alkynyloxy)carbonyl (C1–C3 alkoxy)carbonyl C1–C3 alkyl group, (C3–C8 cycloalkoxy)carbonyl (C1–C3 alkoxy) carbonyl C1–C3 alkyl group, optionally substituted aryloxycarbonyl C1–C3 alkyl group, optionally substituted aryl (C1–C3 alkoxy)carbonyl C1–C3 alkyl group, (C1–C6 alkoxy)carbonyl group, or a group given by the formula $—SO_2R^{17}$, $—C(R^{28})R^{29}CON(R^{21})R^{22}$, $—C(R^{30})R^{31}COON(R^{23})R^{24}$

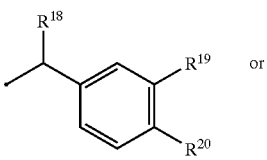 or

-continued

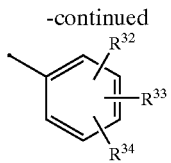

; $R^7$ represents hydrogen atom, C1–C6 alkyl group, C1–C6 haloalkyl group, C3–C8 cycloalkyl group, hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, carboxy C1–C3 alkoxy group, (C1–C6 alkoxy)carboxy C1–C3 alkoxy group, (C3–C8 cycloalkoxy)carboxy C1–C3 alkoxy group, (C3–C6 alkenyloxy)carboxy C1–C3 alkoxy group, (C3–C6 alkynyloxy)carboxy C1–C3 alkoxy group, optionally substituted phenoxy group, optionally substituted benzyloxy group, or a group given by the formula —N($R^{21}$)$R^{22}$ or —ON($R^{23}$)$R^{24}$; R8 represents hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, optionally substituted phenoxy group, optionally substituted benzyloxy group, or a group given by the general formula —N($R^{21}$)$R^{22}$ or —ON($R^{23}$)$R^{24}$; $R^9$ represents hydrogen atom or halogen atom; $R^{10}$ represents hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, optionally substituted phenoxy group, optionally substituted benzyloxy group, or a group given by the general formula —N($R^{21}$)$R^{22}$ or —ON($R^{23}$)$R^{24}$; $R^{11}$ represents hydrogen atom or halogen atom; $R^{12}$ represents hydrogen atom, formyl group, cyano group, nitro group, amino group, C1–C6 alkyl group, C1–C6 haloalkyl group, hydroxy C1–C3 alkyl group, (C1–C3 alkoxy) C1–C3 alkyl group, (C1–C6 alkyl)carbonyloxy C1–C3 alkyl group, (C1–C6 haloalkyl)carbonyloxy C1–C3 alkyl group, carboxy group, (C1–C6 alkoxy)carbonyl group, (C1–C6 haloalkoxy)carbonyl group, (C3–C8 cycloalkoxy)carbonyl group, (C3–C6 alkenyloxy)carbonyl group, (C3–C6 alkynyloxy)carbonyl group or C1–C3 alkoxy (C1–C3 alkoxy)carbonyl group; $R^{13}$ represents hydrogen atom or C1–C3 alkyl group; $R^{14}$ represents hydrogen atom, C1–C6 alkyl group, C1–C6 haloalkyl group, hydroxy C1–C3 alkyl group, (C1–C3 alkoxy) C1–C3 alkyl group, (C1–C6 alkyl)carbonyloxy C1–C3 alkyl group, (C1–C6 haloalkyl)carbonyloxy C1–C3 alkyl group, carboxy group, (C1–C6 alkoxy)carbonyl group, (C1–C6 haloalkoxy)carbonyl group, (C3–C8 cycloalkoxy)carbonyl group, (C3–C6 alkenyloxy)carbonyl group, (C3–C6 alkynyloxy)carbonyl group or C1–C3 alkoxy (C1–C3 alkoxy)carbonyl group; $R^{15}$ represents C1–C6 alkyl group, C1–C6 haloalkyl group, C3–C8 cycloalkyl group, (C3–C8 cycloalkyl) C1–C3 alkyl group, C3–C6 alkenyl group, C3–C6 alkynyl group, cyano C1–C3 alkyl group, (C1–C3 alkoxy) C1–C3 alkyl group, (C1–C3 alkylthio) C1–C3 alkyl group, (C1–C6 alkyl)carbonyl group, (C1–C6 haloalkyl)carbonyl group, (C3–C8 cycloalkyl)carbonyl group, carboxy C1–C3 alkyl group, (C1–C6 alkoxy)carbonyl C1–C3 alkyl group, (C1–C6 haloalkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, C1–C3 alkoxy (C1–C3 alkoxy)carbonyl C1–C3 alkyl group, carboxy (C1–C3 alkoxy)carbonyl C1–C3 alkyl group, (C1–C6 alkoxy)carbonyl (C1–C3 alkoxy)carbonyl C1–C3 alkyl group, (C1–C6 haloalkoxy)carbonyl (C1–C3 alkoxy) carbonyl C1–C3 alkyl group, (C3–C8 cycloalkoxy)carbonyl (C1–C3 alkoxy)carbonyl C1–C3 alkyl group, (C3–C6 alkenyloxy)carbonyl (C1–C3 alkoxy)carbonyl C1–C3 alkyl group, (C3–C6 alkynyloxy)carbonyl (C1–C3 alkoxy) carbonyl C1–C3 alkyl group, optionally substituted aryloxycarbonyl C1–C3 alkyl group, optionally substituted aryl (C1–C3 alkyloxy)carbonyl C1–C3 alkyl group, (C1–C6 alkoxy)carbonyl group or a group given by the formula:

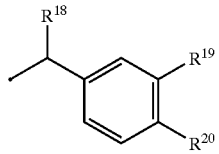

wherein $R^{17}$ represents C1–C3 alkyl group or C1–C3 haloalkyl group; $R^{18}$ represents hydrogen atom, C1–C3 alkyl group or (C1–C6 alkoxy)carbonyl group; $R^{19}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{20}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{21}$ and $R^{22}$ independently represent hydrogen atom or C1–C3 alkyl group, or combined together at their terminal ends to form C2–C5 alkylene group or C1–C3 alkyleneoxy C1–C3 alkylene group; $R^{23}$ and $R^{24}$ independently represent hydrogen atom or C1–C3 alkyl group, or combined together at their terminal ends to form C2–C5 alkylene group or (C1–C3 alkyleneoxy) C1–C3 alkylene group; $R^{25}$ represents hydrogen atom, C1–C3 alkyl group or (C1–C6 alkoxy)carbonyl group; $R^{26}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{27}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{28}$ represents hydrogen atom or C1–C3 alkyl group; $R^{29}$ represents hydrogen atom or C1–C3 alkyl group; $R^{30}$ represents hydrogen atom or C1–C3 alkyl group; $R^{31}$ represents hydrogen atom or C1–C3 alkyl group; $R^{32}$, $R^{33}$ and $R^{34}$ are the same or different and represent hydrogen atom, halogen atom, C1–C3 alkyl group, C1–C3 haloalkyl group, nitro group, amino group, hydroxy group, mercapto group, cyano group, carboxy group, (C1–C6 alkoxy)carbonyl group, (C3–C8 cycloalkoxy)carbonyl group, (C3–C6 alkenyloxy) carbonyl group, (C3–C6 alkynyloxy)carbonyl group, carboxy C1–C3 alkyl group, (C1–C6 alkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group, (C3–C6 alkynyloxy)carbonyl C1–C3 alkoxy group, carboxy C1–C3 alkylthio group, (C1–C6 alkoxy)carbonyl C1–C3 alkylthio group, (C3–C8 cycloalkoxy)carbonyl C1–C3 alkylthio group, (C3–C6 alkenyloxy)carbonyl C1–C3 alkylthio group, (C3–C6 alkynyloxy)carbonyl C1–C3 alkylthio group, carboxy C1–C3 alkylamino group, (C1–C6 alkoxy) carbonyl C1–C3 alkylamino group, (C3–C8 cycloalkoxy) carbonyl C1–C3 alkylamino group, (C3–C6 alkenyloxy) carbonyl C1–C3 alkylamino group, (C3–C6 alkynyloxy) carbonyl C1–C3 alkylamino group, C1–C6 alkoxy group, C3–C6 alkenyloxy group, C3–C6 alkynyloxy group, (C1–C6 alkyl)carbonyloxy group, (C1–C6 alkoxy) carbonyloxy group, C1–C6 alkylthio group, C3–C6 alkenylthio group, C3–C6 alkynylthio group, (C1–C6 alkyl) carbonylthio group, (C1–C6 alkoxy)carbonylthio group, C1–C6 alkylamino group, C3–C6 alkenylamino group, C3–C6 alkynylamino group, (C1–C6 alkyl)carbonylamino group or (C1–C6 alkoxy)carbonylamino group.

2. The 5,6-dihydrouracil compound described in claim 1, wherein Q is a group given by Q1.

3. The 5,6-dihydrouracil compound described in claim 1, wherein Q is a group given by Q4, Q5, Q6, Q7 or Q8.

4. The 5,6-dihydrouracil compound described in claim 1, wherein Q is a group given by Q5, Z is oxygen atom or sulfur atom, $R^1$ is trifluoromethyl group, $R^3$ is fluorine atom and $R^4$ is chlorine atom and $R^6$ is C1–C6 alkyl group, C3–C8 cycloalkyl group, C3–C6 alkenyl group or C3–C6 alkynyl group or (C1–C6 alkoxy)carbonyl C1–C3 alkyl group.

5. The 5,6-dihydrouracil compound described in claim 1, wherein Q is a group given by Q6, $R^1$ is trifluoromethyl group, $R^3$ is fluorine atom and $R^4$ is chlorine atom and $R^7$ is C1–C6 alkoxy group.

6. The 5,6-dihydrouracil compound described in claim 1, wherein Q is a group give Q1, Z is sulfur atom, T is direct bond, $R^1$ is trifluoromethyl group, $R^3$ fluorine atom and $R^{15}$ is C1–C6 alkyl group, C3–C8 cycloalkyl group, C3–C6 alkenyl group or C3–C6 alkynyl group.

7. The 5,6-dihydrouracil compound described in claim 1, wherein Q is a group given by Q1, Z is oxygen atom, T is methylene group, $R^1$ is trifluoro methyl group, $R^3$ is fluorine atom and $R^{15}$ is C1–C6 alkyl group, C3–C8 cycloalkyl group, C3–C6 alkenyl group or C3–C6 alkynyl group.

8. The 5,6-dihydrouracil compound described in claim 1, wherein Q is a group by Q5, Z is oxygen atom, $R^1$ is trifluoromethyl group, $R^3$ is fluoine atom and $R^4$ is chlorine atom and $R^6$ is 1–ethoxycarbonylethyl group.

9. The 5,6-dihydrouracil compound described in claim 1, wherein Q is a group given by Q5, Z is oxygen atom, $R^1$ is trifluoromethyl group, $R^3$ is flourine atom and $R^4$ is chlorine atom and $R^6$ is ethoxycarbonyl group.

10. The 5,6-dihydrouracil compound described in claim 1, wherein Q is a group given by Q5, Z is sulfur atom, $R^1$ is trifluoromethyl group, $R^3$ is fluorine atom and $R^4$ is chlorine atom and $R^6$ is methoxycarbonylmethyl group.

11. The 5,6-dihydrouracil compound described in claim 1, wherein Q is a group given by Q6, $R^1$ is trifluoromethyl group, $R^3$ is fluorine atom and $R^4$ is chlorine atom and $R^7$ is isopropoxy group.

12. The 5,6-dihydrouracil compound described in claim 1, wherein Q is a group given by Q5, Z is oxygen atom, $R^1$ is trifluoromethyl group, $R^3$ is fluorine atom and $R^4$ is chlorine atom and $R^6$ is 1-methoxycarbonylethyl group.

13. The 5,6-dihydrouracil compound described in claim 1, wherein Q is a group given by Q1, Z is sulfur atom, T is direct bond, $R^1$ is trifluoromethyl group $R^3$ is fluorine atom and $R^{15}$ is isopropyl group.

14. The 5,6-dihydrouracil compound described in claim 1, wherein Q is a group given by Q5, Z is oxygen atom, $R^1$ is trifluoromethyl group, $R^3$ is fluorine atom and $R^4$ is chlorine atom and $R^6$ is propargyl group.

15. The 5,6-dihydrouracil compound described in claim 1, wherein Q is a group given by Q1, Z is oxygen atom, T is methylene group, $R^1$ is trifluoromethyl group, $R^3$ is fluorine atom and $R^{15}$ is propargyl group.

16. A herbicidal composition comprising a 5,6-dihydrouracil compound which is described in claim 1 as an active ingredient and a carrier.

17. A method for controlling weeds which comprises applying an effective amount of a 5,6-dihydrouracil compound which is described in claim 1 to weeds or a place where weeds grow or will grow.

* * * * *